(12) United States Patent
Makriyannis et al.

(10) Patent No.: US 7,589,220 B2
(45) Date of Patent: Sep. 15, 2009

(54) INHIBITORS OF THE ANANDAMIDE TRANSPORTER

(75) Inventors: Alexandros Makriyannis, Mystic, CT (US); Andreas Goutopoulos, Boston, MA (US); Chen Li, Willimantic, CT (US)

(73) Assignee: University of Connecticut, Farmington, CT (US)

( * ) Notice: Subject to any disclaimer, the term of this patent is extended or adjusted under 35 U.S.C. 154(b) by 590 days.

(21) Appl. No.: 10/899,191

(22) Filed: Jul. 26, 2004

(65) Prior Publication Data

US 2005/0020679 A1 Jan. 27, 2005

Related U.S. Application Data

(63) Continuation-in-part of application No. 09/701,989, filed as application No. PCT/US99/12900 on Jun. 9, 1999, now abandoned.

(60) Provisional application No. 60/088,568, filed on Jun. 9, 1998.

(51) Int. Cl.
*C07C 233/00* (2006.01)
(52) U.S. Cl. .......................... 554/61; 514/548
(58) Field of Classification Search ............ 554/61; 514/548
See application file for complete search history.

(56) References Cited

U.S. PATENT DOCUMENTS

| | | |
|---|---|---|
| 3,041,343 A | 6/1962 | Jucker et al. |
| 3,465,024 A | 9/1969 | Brownstein et al. |
| 3,573,327 A | 3/1971 | Miyano |
| 3,577,458 A | 5/1971 | Brownstein et al. |
| 3,656,906 A | 4/1972 | Bullock |
| 3,838,131 A | 9/1974 | Gauthier |
| 3,886,184 A | 5/1975 | Matsumoto et al. |
| 3,897,306 A | 7/1975 | Vidic |
| 3,915,996 A | 10/1975 | Wright |
| 3,928,598 A | 12/1975 | Archer |
| 3,944,673 A | 3/1976 | Archer |
| 3,946,029 A | 3/1976 | Descamps et al. |
| 3,953,603 A | 4/1976 | Archer |
| 4,036,857 A | 7/1977 | Razdan et al. |
| 4,054,582 A | 10/1977 | Blanchard et al. |
| 4,087,545 A | 5/1978 | Archer et al. |
| 4,087,546 A | 5/1978 | Archer et al. |
| 4,087,547 A | 5/1978 | Archer et al. |
| 4,088,777 A | 5/1978 | Archer et al. |
| 4,102,902 A | 7/1978 | Archer et al. |
| 4,152,450 A | 5/1979 | Day et al. |
| 4,171,315 A | 10/1979 | Ryan et al. |

(Continued)

FOREIGN PATENT DOCUMENTS

EP 0276732 8/1988

(Continued)

OTHER PUBLICATIONS

Lin et al ( J. Med. Chem.; vol. 41, 5353, 1997).*

(Continued)

*Primary Examiner*—Deborah D Carr
(74) *Attorney, Agent, or Firm*—Alix, Yale & Ristas, LLP

(57) ABSTRACT

Disclosed are compounds that are anandamide transport inhibitors and their pharmacological use.

7 Claims, 2 Drawing Sheets

U.S. PATENT DOCUMENTS

| | | | |
|---|---|---|---|
| 4,176,233 A | 11/1979 | Archer et al. | |
| 4,179,517 A | 12/1979 | Mechoulam | |
| 4,188,495 A | 2/1980 | Althuis et al. | |
| 4,208,351 A | 6/1980 | Archer et al. | |
| 4,278,603 A | 7/1981 | Thakkar et al. | |
| 4,282,248 A | 8/1981 | Mechoulam et al. | |
| 4,382,943 A | 5/1983 | Winter et al. | |
| 4,395,560 A | 7/1983 | Ryan | |
| 4,550,214 A | 10/1985 | Mehta | |
| 4,758,597 A | 7/1988 | Martin et al. | |
| 4,812,457 A | 3/1989 | Narumiya | |
| 4,876,276 A | 10/1989 | Mechoulam | |
| 4,885,295 A | 12/1989 | Bell et al. | |
| 5,053,548 A | 10/1991 | Tanaka et al. | |
| 5,068,234 A | 11/1991 | D'Ambra et al. | |
| 5,147,876 A | 9/1992 | Mizuchi et al. | |
| 5,223,510 A | 6/1993 | Gubin et al. | |
| 5,284,867 A | 2/1994 | Kloog | |
| 5,324,737 A | 6/1994 | D'Ambra et al. | |
| 5,434,295 A | 7/1995 | Mechoulam et al. | |
| 5,440,052 A | 8/1995 | Makriyannis et al. | |
| 5,462,960 A | 10/1995 | Barth et al. | |
| 5,489,580 A | 2/1996 | Makriyannis et al. | |
| 5,521,215 A | 5/1996 | Mechoulam | |
| 5,532,237 A | 7/1996 | Gallant et al. | |
| 5,538,993 A | 7/1996 | Mechoulam | |
| 5,576,436 A | 11/1996 | McCabe et al. | |
| 5,605,906 A | 2/1997 | Lau | |
| 5,607,933 A | 3/1997 | D'Ambra et al. | |
| 5,618,955 A | 4/1997 | Mechoulam et al. | 554/66 |
| 5,624,941 A | 4/1997 | Barth et al. | |
| 5,631,297 A | 5/1997 | Pate et al. | |
| 5,635,530 A | 6/1997 | Mechoulam | |
| 5,688,825 A | 11/1997 | Makriyannis et al. | |
| 5,744,459 A | 4/1998 | Makriyannis et al. | |
| 5,747,524 A | 5/1998 | Cullinan et al. | |
| 5,804,601 A | 9/1998 | Kato et al. | |
| 5,817,651 A | 10/1998 | D'Ambra et al. | |
| 5,872,148 A | 2/1999 | Makriyannis et al. | |
| 5,874,459 A | 2/1999 | Makriyannis et al. | |
| 5,925,628 A | 7/1999 | Lee et al. | |
| 5,925,768 A | 7/1999 | Barth et al. | |
| 5,932,610 A | 8/1999 | Shohami et al. | |
| 5,939,429 A | 8/1999 | Kunos et al. | |
| 5,948,777 A | 9/1999 | Bender et al. | |
| 6,013,648 A | 1/2000 | Rinaldi et al. | |
| 6,028,084 A | 2/2000 | Barth et al. | |
| 6,096,740 A | 8/2000 | Mechoulam | |
| 6,127,399 A | 10/2000 | Yuan | |
| 6,166,066 A | 12/2000 | Makriyannis et al. | |
| 6,284,788 B1 | 9/2001 | Mittendorf et al. | |
| 6,391,909 B1 | 5/2002 | Makriyannis et al. | |
| 6,579,900 B2 | 6/2003 | Makriyannis et al. | |
| 6,610,737 B1 | 8/2003 | Garzon et al. | |
| 2002/0119972 A1 | 8/2002 | Leftheris et al. | |
| 2002/0173528 A1 | 11/2002 | Fride et al. | |
| 2003/0120094 A1 | 6/2003 | Makriyannis et al. | |
| 2003/0149082 A1 | 8/2003 | Makriyannis et al. | |
| 2004/0077649 A1 | 4/2004 | Makriyannis et al. | |
| 2004/0077851 A1 | 4/2004 | Makriyannis et al. | |
| 2004/0087590 A1 | 5/2004 | Makriyannis et al. | |
| 2004/0192667 A1 | 9/2004 | Makriyannis et al. | |
| 2004/0236101 A1 | 11/2004 | Makriyannis et al. | |
| 2004/0236116 A1 | 11/2004 | Makriyannis et al. | |

FOREIGN PATENT DOCUMENTS

| | | | |
|---|---|---|---|
| EP | 0444451 | | 9/1991 |
| EP | 0471609 | | 6/1993 |
| EP | 0576357 | | 12/1993 |
| EP | 0737671 | | 10/1996 |
| EP | 0860168 | | 9/2001 |
| FR | 2240003 | | 5/1975 |
| FR | 2735774 | | 1/2000 |
| GB | 2027021 A | | 2/1980 |
| IL | 1995-113228 | | 9/1999 |
| JP | 57098228 | | 6/1982 |
| JP | 2304080 | | 12/1990 |
| NL | 6509930 | * | 2/1966 |
| WO | WO 94/12466 | | 6/1994 |
| WO | WO 97/00860 | | 1/1997 |
| WO | WO 97/21682 | | 6/1997 |
| WO | WO 97/45407 A | | 12/1997 |
| WO | WO 99/57106 | | 11/1999 |
| WO | WO 99/57107 | | 11/1999 |
| WO | WO 00/32200 | | 6/2000 |
| WO | WO 01/28329 | | 4/2001 |
| WO | WO 01/28497 | | 4/2001 |
| WO | WO 01/28498 | | 4/2001 |
| WO | WO 01/28557 | | 4/2001 |
| WO | WO 01/29007 | | 4/2001 |
| WO | WO 01/32169 | | 5/2001 |
| WO | WO 01/58869 | | 8/2001 |
| WO | WO 02/12167 | | 2/2002 |
| WO | WO 02/058636 | | 8/2002 |
| WO | WO 02/060447 | | 8/2002 |
| WO | WO 03/005960 | | 1/2003 |
| WO | WO 03/020217 | | 3/2003 |
| WO | WO 03/035005 | | 5/2003 |
| WO | WO 03/063758 | | 8/2003 |
| WO | WO 03/064359 | | 8/2003 |

OTHER PUBLICATIONS

Berglund et al (Prostaglandins, Leukotrienes, and Essential Fatty Acids, 59(2), 111-118; 1998).*

Zhong et al (International Journal of Chemical Kinetics (1997), 29(12), 893-913).*

Ng et al; "Unique Analogues of Anandamide: Arachidonyl Ethers and Carbamates and Norarachidonyl Carbamates and Ureas"; J. Med. Chem.; 1999; 42(11); 1975-1981.

Mechoulam, R. et al, "Towards cannabinoid drugs—revisited" Progress in Medicinal Chemistry, Elsevier, Amsterdam, NL, vol. 35, Jul. 3, 1998, pp. 199-243.

Twitchell, W. et al; "Cannabinoids inhibit N- and P/Q type calcium channels in cultured rat hippocampal neurons"; Journal of Neurophysiology; 78(1); 43-50; 1997 (abstract only).

Ueda, N., Endocannabinoid hydrolases. Prostaglandins & Other Lipid Mediators 2002;68-69:521-534 (abstract only).

Vogel Z., Barg J., Levy R., Saya D., Heldman E., Mechoulam R.; "Anandamide, a brain endogenous compound, interacts specifically with cannabinoid receptors and inhibits adenylate cyclase"; J. Neurochem.; 61(1) 352-355; (1993) (abstract only).

Wagner JA, Varga K, Jarai Z, Kunos G; "Mesenteric Vasodilation Mediated by Endothelia Anandamide Receptors"; Hypertension (1999) 33:429-434.

Watanabe, T.; Miyaura, N.; and Suzuki, A.; "Synthesis of Sterically Hindered Biaryls via the Palladium Catalyzed Cross-Coupling Reaction of Arylboronic Acids or their Esters with Haloarenes"; Synlett 1992, 207-210.

Wiley et al; "Structure activity relationships of indole and pyrrole derived cannabinoids"; J. Pharmacol. Exp. Ther. 1998, 285(3), 995-1004; XP-001097982.

Wilson et al; "9-nor-delta8-tetrahydrocannabinol, a cannabinoid of metabolic intersts"; J. Med. Chem.; 17(4); 475-476; (1974).

Wilson et al; "Analgesic properties of the tetrahydrocannabinols, their metabolites and analogs"; J. Med. Chem.; 18(7); 700-703; (1975).

Wilson et al; "9-nor-9-hydrohexahydrocannabinols. Synthesis, some behavioral and analgesic properties, and comparison with the tetrahydrocannabinols"; J. Med. Chem.; 19(9); 1165-1167; (1976).

Yamada et al; "(Aminoalkyl)indole isothiocyanates as potentital electrophilic affinity ligands for the brain cannabinoid receptor"; J. Med. Chem. 1996, vol. 39(10), 1967-1974.

Yan, Guo et al; "Synthesis and pharmacological properties of 11-hydroxy-3-(1'-1'-dimethylheptyl)hexahydrocannabinol: a high affinity cannabinoid agonist"; J. Med. Chem.; vol. 37(16); 2619-2622; (1994).

Yan Guo et al; "(-)-11-hydroxy-7'-isothiocyanato-1'-1'dimethylheptyl-delta8-THC: a novel probe for the cannabinoid receptor in the brain"; J. Med. Chem.; 37(23); 3867-3870; (1994).

Abadji V., Lin S., Taha G., Griffin G., Stevenson L.A., Pertwee R.G., Makriyannis A.; "(R)-Methanadamide: a chiral novel anandamide possessing higher potency and metabolic stability"; J. Med. Chem.; 37(12); 1889-1893; 1994; CODEN: JMCMAR; ISSN: 0022-2623; XP002040932.

Alo, B.I.; Kandil, A.; Patil, P. A.; Sharp, M. J.; Siddiqui, M. A.; and Snieckus, V. Sequential Directed Ortho Metalation-Boronic Acid Cross-Coupling Reactions. A general Regiospecific Route to Oxygenated Dibenzo[b,d]pyran-6-ones Related to Ellagic Acid, J. Org. Chem. 1991, 56, 3763-3768.

Archer et al; "cannabinoids, synthesis approaches to 9-ketocannabinoids."; J. Org. Chem.; vol. 42; No. 13; 2277-2284; (1977).

Arnone M., Maruani J., Chaperon P, et al, Selective inhibition of sucrose and ethanol intake by SR141716, an antagonist of central cannabinoid (CB1) receptors, Psychopharmacal, (1997) 132, 104-106. (abstract only).

Barnett-Norris et al; "Exploration of biologically relevant conformations of anandamide, . . . "; J. Med. Chem.; vol. 41; 4861-4872; 1998.

Beak, P.; and Brown, R A., The Tertiary Amide as an Effective Director of Ortho Lithiation, J. Org. Chem. 1982, 47, 34-36.

Belgaonkar et al; "synthesius of isocoumarins"; Indian J. Chem; vol. 13; No. 4; 336-338; 1975 (abstract only).

Beltramo M., Stella N., Calignano A., Lin S. Y., Makriyannis A., Piomelli D; "Identification and Functional Role of High Affinity Anandamide Transport"; The Neurosciences Institute (1 page).

Beltramo M., Piomelli D; "Anandamide Transport Inhibition by the Vanilloide Agonist Olvanil"; Europeean J. of Pharmacology; (1999); 364(1); 75-78 (abstract only).

Berdyshev EV, Cannabinoid receptors and the regulation of immune response. Chem Phys Lipids. Nov. 2000; 108(1-2):169-90.

Berglund et al; "Structural requirements for arachidonylethanolamide interaction with CB1 and CB2 cannabinoid receptors: . . . "; Prostanglandins, leukotrienes ands essential fatty acids; 59(2); 111-118; (1998).

Bodnar, V.N., Lozinskii, M.O., Pel'kis, P.S.; "Synthesis fo 2,5-disubstituted 1,3,4-oxadiazoles and 1,4-dihydro-1,2,4,5-tetrazines"; Ukrainskii Khimicheskii Zhurnal (Russian Edition); 48(12); 1308-1311; 1982 (abstract only).

Bracey, M et al, Structural Adaptations in a Membrane Enzyme That Terminates Endocannabinoid Signaling. Science 2002; 298(5599): 1793-1796.

Brenneisen R, Pgli A, Elsohly MA, Henn V. Spiess Y: The effect of orally and rectally administered Δ9—tetrahydrocannabinol on spasticity, a pilot study with 2 patients. Int. J. Clin Pharmacol Ther. (1996) 34:446-452. (abstract only).

Brotchie JM: Adjuncts to dopamine replacement a pragmatic approach to reducing the problem of dyskinesia in Parkinson's disease. Mov. Disord. (1998)13:871-876. (abstract only).

Brown et al; "Synthesis and hydroboration of (-)-2-phenylapopinene, Comparison of mono(2-phenylapoisopinocampheyl)borane with its 2-methyl and 2-ethyl analogues for the chiral hydroboration of representative alkenes"; J. Org. Chem.; 55(4); 1217-1223; (1990).

Buckley NE, McCoy KI, Mpzey E et al, "Immunomodulation by cannabinoids is absent in mice deficient for the cannabinoid CB2 receptor"; Eur. J Pharmacol (2000) 396:141-149.

Burstein et al; "detection of cannabinoid receptors . . . "; Biochem. Biophys. Res. Commun.; vol. 176(1); 492-497; 1991 (abstract only).

Busch-Peterson et al; "Unsaturated side chain beta-11-hydroxyhexahydrocannabinol analogs"; J. Med. Chem; 39; 3790-3796; (1996).

Calignano A, La Rana G. Diuffrida A, Piomelli D; "Control of pain initiation by endogenous cannabinoids"; Nature (1998) 394:277-291. (abstract only).

Campbell FA et al; "Are cannabinoids an effective and safe treatment option in the management of pain? A qualitative systematic review"; BMJ. Jul. 7, 2001;323(7303):13-6.

Charalambous A. et al; "5'-azido Δ8-THC: A Novel Photoaffinity Label for the Cannabinoid Receptor"; J. Med. Chem., 35, 3076-3079 (1992).

Charalambous A. et al; "Pharmacological evaluation of halogenated . . . "; Pharmacol. Biochem. Behav.; vol. 40; No. 3; 509-512; 1991.

Cheng et al; "Relationship Between the Inhibition Constant (Ki) and the concentration of Inhibitor which causes 50% Inhibition (IC50) of an Enzymatic Reaction"; Biochem. Pharmacol., 22, 3099-3102, (1973) (abstract only).

Cherest M., Luscindi X.; "The action of acetyl chloride and of acetic anhydride on the lithium nitronate salt of 2-phenylnitroethane . . . "; Tetrahedron; 42(14); 3825-3840; 1986; in French with English abstract.

Cherest M., Lusinchi X.; "A novel electrophilic N-amidation via electron deficient complexes: action of ferric chloride on N-acetyloxyamides"; Tetrahedron Letters; 30(6); 715-718; 1989.

Colombo G, Agabio R, Diaz G. et al; "Appetite suppression and weight loss after the cannabinoid antagonist SR141716"; Life Sci. (1998) 63-PL13-PL117. (abstract only).

Compton D.R. et al; "Pharmacological Profile Of A Series Of Bicyclic Cannabinoid Analogs: Classification as Cannabimimetic Agents"; J. Pharmacol. Exp. Ther.; 260; 201-209; 1992. (abstract only).

Compton et al; "Synthesis and pharmacological evaluation of ether and related analogues of delta8-. delta9- and delta9,11-tetrahydrocannabinol"; J. Med. Chem; vol. 34; No. 11; 3310-3316; 1991.

Consroe P, Musty R, Rein J, Tillery W, Pertwee R; "The perceived effects of smoked cannabis on patents with multiple sclerosis"; Eur. Neurol. (1997) 38-44-48. (abstract only).

Coxon et al; "Derivatives of nopinone"; Aust. J. Chem.; 23; 1069-1071; (1970) (abstract only).

Crawley et al; "Anandamide, an endogenous ligand of the cannabinoid receptor, induces hypomotility and hypothermia in vivo in rodents"; Pharmacology Biochemistry and Behavior; vol. 46; 967-972; 1993.

D'Ambra et al; "C-attached aminoalkylindoles: potent cannabinoid mimetics"; Bioorg. & Med. Chem. Lett., 1996, 6(1), 17-22.

D'Amour F.E. et al; "A Method For Determining Loss Of Pain Sensation"; J. Pharmacol. Exp. Ther.; 72; 74-79; 1941.

Demuynck L. et al; "Rearrangement of Indolo[2,3-a]quinolizidines to derivatives with E-azaaspidospermane skeleton"; Tetrahedron Letters; 30(6) 710-722; 1989; in French with English abstract.

DePetrocellis L, Melck D, Palmisano A. et al; "The endogenous cannabinoid anandamide inhibits human breast cancer cell proliferation"; Proc. Natl. Acad. Sci. USA (Jul. 1998) 95:8375-8380.

Desarnaud F., Cadas H., Piomelli D.; "Anandamide amidohydrolase activity in rat brain microsomes"; J. Biol. Chem.; 270; 6030-6035; (1995).

Deutsch D.G. et al; "Fatty acid sulfonyl fluorides inhibit anandamide metabolism and bind to cannabinoid receptor"; Biochem. Biophys. Res. Commun. 231(1); 217-221; 1997; CODEN: BBRCA9; ISSN:0006-291X; XP002040933.

Deutsch D.G., Chin S.A.; "Enzymatic synthesis and degradation of anandamide, a cannabinoid receptor agonist"; Biochemical Pharmacology; 46(5); 791-796; 1993.

Devane, W.A. et al; "Determination and Characterization of a Cannabinoid Receptor in a Rat Brain"; Mol. Pharmacol., 34, 605-613 (1988). (abstract only).

Di Marzo, V., Melck, D., Bisogno, T., DePetrocellis, L.; "Endocannabinoids: endogenous cannabinoid receptor ligands with neuromodulatory action"; Trends Neurosci. (1998) 21:521-528.

Di Marzo, V., Bisogno, T., Melck, D., Ross, R., Brockie, H., Stevenson, L., Pertwee, R., DePetrocellis, L., "Interactions between synthetic vanilloids and the endogenous cannabinoid system"; FEBS Letters; (1998); 437(3); 449-454. (abstract only).

Dodd, P.R. et al, A Rapid Method for Preparing Synaptosomes: Comparison with Alternative Procedures, Brain Res., 226, 107-118 (1981). (abstract only).

Dominiami et al; "Synthesis of 5-(tert-Alkyl)resorcinols"; J. Org. Chem. 42(2); 344-346; (1977).

Drake et al, "classical/nonclassical hybrid cannabinoids"; J. Med. Chem.; vol. 41(19); 3596-3608 (1998).

Edery et al; "Activity of novel aminocannabinoids in baboons"; J. Med. Chem.; 27; 1370-1373 (1984).

Eissenstat et al; "Aminoalkylindoles: structure-activity relationships of novel cannabinoid mimetics"; J. Med. Chem. 1995, vol. 38, No. 16, pp. 3094-3105; XP 000651090.

Fahrenholtz, K. E., Lurie, M. and Kierstead, AR. W.; "The Total Synthesis of dl-Δ9-Tetrahydrocannabinol and Four of Its Isomers"; J. Amer. Chem. Soc. 1967, 89(23), 5934-5941.

Fahrenholtz; "The synthesis of 2 metabolites of (-)-delta eight-tetrahydrocannabinol"; J. Org. Chem.; vol. 37(13); 1972; XP002111824.

Fisera, L., Kovac, J., Lesco, J., Smahovsky, V.; "Furan derivatives. Part CLVI. 1,3-dipolar cycloadditions of heterocycles. V. Reaction of C-acetyl-N-phenylnitrilimine with furan derivatives"; Chemicke Zvesti; 35(1); 93-104 1981 (abstract only).

Fride, E. & Mechoulam, R.; "Pharmacological activity of the cannabinoid receptor agonist, anandamide, a brain constituent"; European Journal of Pharmacology, vol. 231; 313-314; 1993.

Galiegue S et al.; "Expression of central and peripheral cannabinoid receptors in human immune tissues and leukocyte subpopulations"; Eur J Biochem.; Aug. 15, 1995;232(1):54-61. (abstract only).

Gareau, Y.; Dufresne, C.; Gallant, M.; Rochette, C.; Sawyer, N.; Slipetz, D. M.; Tremblay, N.; Weech, P. K.; Metters, K. M.; Labelle, M.; "Structure activity relationships of tetrahydrocanabinol analogs on human cannabinoid receptors"; Bioorg. Med. Chem. Lett. 1996, 6(2), 189-194.

Gold et al; "A comparison of the discriminative stimulus properties of delta9-tetrahydrocannabinol and CP 55,940 in rats and rhesus monkeys"; J. Pharmacol. Exp. Ther.; vol. 262(2); 479-486; 1992.

Green K.; "Marijuana smoking vs. cannabinoids for glaucoma therapy."; Arch. Ophthamol. (1998) Nov. 116(11); 1433-1437. (abstract only).

Griffin, G., Wray, E. J., Tao, Q., McAllister, S. D., Rorrer, W. K., Aung, M., Martin, B. R., Abood, M. E.; "Evaluation of the cannabinoid CB2 receptor selective antagonist, SR144528: further evidence for cannabinoid CB2 receptor absence in the rat central nervous system"; European Journal of Pharmacology; (1999); vol. 377; 117-125.

Hampson, A.J., Grimaldi M. Axpirod J. Wink D; "Cannabidiol and (-) Δ9 tetrahydrocannabinol are neuroprotective antioxidants"; Proc. Natl Acad Sci. USA (Jul. 1998) 95; 8268-8273.

Hanus et al; "Two new unsaturated fatty acid ethanolamides in brain that bind to the cannabinoid receptor"; Journal of medicinal Chemistry; 36(20); 3032-3034; 1993.

Hargreaves, K. et al; "A new sensitive method for measuring thermal nociception in cutaneous hyperalgesia"; Pain; 32; 77-88; (1988) (abstract only).

Hemming M, Yellowlees PM; "Effective treatment of Tourette's syndrome with marijuana"; J. Psychopharmacol, (1993) 7:389-391.

Herzberg U, Eliav E, Bennett GJ, Kopin IJ; "The analgesic effects of R(+) WIN 55,212-2 mesylate, a high affinity cannabinoid agonist in a rat model of neuropathic pain"; Neurosci. Letts. (1997) 221; 157-160.

Horrevoets A.J.G et al; "Inactivation of *Escherichia coli* outer membrane phospholipase A by the affinity label hexadecanesulfonyl fluoride"; Eur. J. Biochem.; 198; 247-253; 1991.

Horrevoets A.J.G et al; "Inactivation of reconstituted *Escherichia coli* outer membrane phospholipase A by membrane-perturbing peptides results in an increased reactivity towards the affinity label hexadecanesulfonyl fluoride"; Eur. J. Biochem.; 198; 255-261; 1991.

Howlett et al; "Azido and isothicyanato substituted aryl pyrazoles bind covalently to the CB1 cannabinoid receptor and impair signal transduction"; Journal of Neurochemistry; vol. 74(5) (2000) 2174-2181; XP001097394.

Howlett et al; "Stereochemical effects of 11-OH-delta 8 tetrahydrocannabinol-dimethylheptyl to inhibit adenylate cyclase and bind to the cannabinoid receptor"; Neuropharmacology; vol. 29(2); 161-165; 1990.

Huffman et al; "3-(1',1'-dimethylbuty1)—deoxy-delta 8THC and related compounds: synthesis of selective ligands for the CB2 receptor"; Bioorganic and Medicinal Chemistry; vol. 7; 2905-2914; (1999).

Huffman et al; "Stereoselective synthesis of the epimeric delta 7-tetrahydocanabinols"; tetrahedron; vol. 51(4); 1017-1032; (1995).

Huffman et al; "Synthesis of 5',11 dihydroxy delta 8 tetrahydrocannabinol"; Tetrahedron, vol. 53(39), pp. 13295-13306 (1997).

Huffman et al; "Synthesis of a tetracyclic, conformationally constrained analogue of delta8-THC"; Bioorganic & Medicinal Chemistry; vol. 6(12); 2281-2288; 1998; XP002123230.

Huffman et al; "Synthesis of both enantiomers of Nabilone from a common intermediate. Enantiodivergent synthesis of cannabinoids"; J. Org. Chem.; 1991, 56, 2081-2086.

Jbilo, O., Derocq, J., Segui, M., Le Fur, G., Casellas, P.; "Stimulation of peripheral cannabinoid receptor CB2 induces MCP-1 and IL-8 gene expression in human promyelocytic cell line HL60"; FEBS Letters; (1999); vol. 448; No. 21848; 273-277.

Joy JE, Wagtson SJ, Benson JA; "Marijuana and Medicine Assessing the Science Base"; National Academy Press, Washington, DC, USA (1999). (abstract only).

Kaminski NE; "Regulation of the cAMP cascade, gene expression and immune function by cannabinoid receptors"; J Neuroimmunol. Mar. 15, 1998;83(1-2):124-32.

Kawase M. et al; "Electrophilic aromatic substitution with N-methoxy-N-acylnitrenium ions generated from N-chloro-N-methoxyamides: synthesis of nitrogen heterocyclic compounds bearing a N-methoxyamide group"; J. Org. Chem.; 54; 3394-3403; 1989.

Khanolkar et al; "Molecular probes for the cannabinoid receptors"; Chemistry and Physics of Lipids; 108; 37-52; (2000).

Klein T.W. et al, "The cannabinoid system and cytokine network"; Proc Soc Exp Biol Med. Oct. 2000; 225(1):1-8; (abstract only).

Klein TW et al, "Cannabinoid receptors and immunity"; Immunol Today; Aug. 1998; 19(8):373-81.

Koutek B. et al; "Inhibitors of arachidonyl ethanolamide hydrolysis"; J. Biol. Chem.; 269(37); 22937-40; 1994; CODEN: JBCHA3; ISSN: 0021-9258; XP002040931.

Kumar RN, et al; "Pharmacological actions and therapeutic uses of cannabis and cannabinoids"; Anesthesia, 2001, 56: 1059-1068 (abstract only).

Lan, R et al; "Structure activity relationships of pyrazole derivatives as cannabinoid receptor antagonists"; J. Med. Chem.; vol. 42(4); 769-776; (1999).

Lang, W., Qin, C., Hill, W.A., Lin, S., Khanolkar, A.D., Makriyannis, A.; High-Performance Liquid Chromatographic Determination Of Anandamide Amidase Activity in Rat Brain Microsomes; Anal. Biochem; (1996), 238, 40-45 (abstract only).

Lang, W. et al; "Substrate Specificity and Stereoselectivity of Rat Brain Microsomal Anandamide Amidohydrolase"; J. Med. Chem.; vol. 42(5); 896-902; (1999).

Lavalle et al; "Efficient conversion of (1R, 5R)-(+)-alpha-pinene to (1S, 5R)-(−)-nopinene"; J. Org. Chem.; vol. 51(8); 1362-1365; (1986).

Lin S., Khanolkar A., Fan P., Goutopolous A., Qin C., Papahadjis D., Makriyannis A.; "Novel Analogues of arachidonylethanolamide (anandamide): affinities for the CB1 and CB2 Cannabinoid Receptors and Metabolic Stability"; J. Med. Chem.; vol. 41; 5353; 1998.

Loev, B., Bender, P. E., Dowalo, F., Macko, E., and Fowler, P.; "Cannabinoids. Structure-Activity Studies Related to 1,2-Dimethylheptyl Derivatives"; J. Med. Chem.; vol. 16(11); 1200-1206; 1973.

Lozinskii, M.O., Bodnar, V.N., Konovalikhin, S.V., D'yachenko, O.A., Atovmyan, L.O.; "Unusual transformations of arylhydrazonoyl chlorides of oxalic acid ethyl ester"; Izvestiya Akademii Nauk SSSr, Seriya Khimicheskaya; 11; 2635-2637; 1990 (abstract only).

Ludt, R.E. et al; "A comparison of the synthetic utility of n-butyllithium and lithium diisopropylamide in the metalations of N,N-dialkyltouamides"; J. Org. Chem.; 38(9); 1668-1674 (1973).

Maccarron M., Endocannabinoids and their actions. *Vitamins and Hormones* 2002;65:225-255.

Mackie K., Devane W.A., Hille B.; "Anandamide, an endogenous cannabinoid, inhibits calcium currents as a partial agonist in N18 neuroblastoma cells"; Mol. Pharmacol; 44; 498-0503 (1993).

Markwell, M.A.K., S.M. Haas, L.L. Bieber, and N.E. Tolbert.; "A modification of the Lowry procedure to simplify protein determination in the membrane and lipoprotein samples." 1978; *Anal. Biochem.* 87:206-210.

Martin et al; "Behavioral, biochemical, and molecular modeling evaluations of cannabinoid analogs"; Pharmacol. Biochem. Behav.; vol. 40(3); 471-478; 1991.

Martyn CN. Illis LS, Thom J.; "Nabilone in the treatment of multiple sclerosis"; Lancet (1995) vol. 345; pp. 579.

Matsumoto et al; "Cannabinoids 1.1-amino-and 1 mercapto-7,8,9,10-tetrahydro-6h-dibenzo[b,d]pyrans"; J. of Med. Chem.; vol. 20(1); 17-24; 1977; XP00211825.

Maurer M, Henn V, Dittrich A, Hofmann A.; "Delta-9-tetrahydrocannabinol shows antispastic and analgesic effects in a single case double-blind trial."; Eur. Arch. Psychiat. Clin. Neurosci. (1990), 240:1-4. (abstract only).

Mavromoustakos, T. et al; "Studies on the thermotropic effects of cannabinoids on phosphatidylcholine bilayers using differential scanning calorimetry and small angle X-ray diffraction"; Biochimica et Biophysica Acta; vol. 1281(2); 1996; XP002111823.

Mechoulam et al; "Stereochemical Requirements for cannabinoid activity"; J. Med. Chem.; 23(10); 1068-1072; (1980).

Mechoulam et al; Structural Requirements for Binding of Anandamide Type Compounds to the Brain Cannabinoid Receptor; J. Med. Chem.; 1997; 40; 659-667.

Mechoulam et al; "Synthesis of the individual, pharmacologically distinct, enantiomers of a tetrahydrocannabinol derivative"; Tetrahedron Asymmetry; 1: 311-314; (1990) (abstract only).

Mechoulam et al; "Synthesis of the individual, pharmacologically distinct, enantiomers of a tetrahydrocannabinol derivative."; *Tetrahedron Asymmetry*; 1: 315-318; (1990).

Mechoulam, "Cannabinoids as therapeutic agents"; *CRC press*, 1986.

Melck, D., Bisogno, T., DePetrocellis, L., Chuang, H., Julius, D., Bifulco, M., DiMarzo, V.; "Unsaturated Long-Chain N-Acyl-vanillyl-amides"; Biochemical and Biophysical Res. Commun.; (1999); 262(1); 275-284 (abstract only).

Meltzer et al; "An improved synthesis of cannabinol and cannabiorcol"; Synthesis; 1981:985 (1981).

Melvin et al; "Structure-Activity Relationships Defining the ACD-Tricyclic Cannabinoids Cannabinoid Receptor Binding and Analgesic Activity"; Drug Design and Discovery; 13(2); 155-166 (1995). (abstract only).

Melvin et al; "Structure-activity relationships for cannabinoid receptor-binding and analgesic activity: studies of bicyclic cannabinoid analogs"; Mol. Pharmacol.; .44(5); 1008-1015 (1993) (abstract only).

Merck Index; 11th edition; "Tetrahydrocannabinols" compound No. 9142; 1989.

Meschler, J. P., Kraichely, D. M., Wilken, G. H., Howlett, A. C.; "Inverse Agonist Properties of N-(Piperidin-1-yl)-5-(4-chlorophenyl)-1-(2,4-dichlorophenyl)-4-methyl-1H-pyrazole-3-carboxamide HCL (SR141716A) and 1-(2-Chlorophenyl)-4-cyano-5-(4-methoxyphenyl)-1H-pyrazole-3-carboxylic Acid Phenylamide (CP-272871) for the CB1 Cannabinoid Receptor"; Biochemical Pharmacology; (2000); vol. 60; No. 9; 1315-1322.

Morgan Dr: *Therapeutic Uses of Cannabis*. Harwood Academic Publishers, Amsterdam. (1997).

Morris, S,; Mechoulam, R.; and Irene, Y., Halogenation of phenols and Phenyl ethers with Potassium Halides in the Presence of 18-Crown-6 on Oxidation with m-Chloroperbenzoic Acid, *J. Chem. Soc., Perkin Trans. 1* 1987, 1423-1427.

Muller-Vahl KB, Kolbe H, Schneider U, Emrich, HM Cannabis in movement disorders. Porsch. Kompicmentarmed (1999) 6 (suppl. 3) 23-27. (abstract only).

Muller-Vahl KB, Schneider U, Kolbe H, Emrich, HM.; "Treatment of Tourette's syndrome with delta-9-tetrahydrocannabinol." Am. J. Psychiat.; (1999); 156(3); 495.

Nahas G, *Marijuana and Medicine*; 1999, Human Press Inc., Totowa, NJ.

Neunhoeffer O., Gottschlich R.; "Acylating activity of O-acylated hydroxylamine derivatives"; Justus Liebigs Ann. Chem.; 736; 100-109; 1970; in German with English abstract.

Novak, J et al; Cannabis, part 27, synthesis of 8-, 10- and 11-oxygenated cannabinoids; J. Chem. Soc. Perkin Trans.; 2867-2871; (1983) (abstract only).

Nye et al; "High affinity cannabinoid binding sites in brain membranes labelled with [H]-5'-trimethylammonium delta8-tetrahydrocannabinol"; J. Pharmacol. Exp. Ther.; vol. 234(3); 784-791; 1985.

Pacheco M, et al; "Aminoalkylindoles: Actions On Specific G-Protein-Linked Receptors"; J. Pharmacol. Exp. Ther.; vol. 257, No. 1, pp. 170-183 and 172 Table (1991).

Palmer et al; "Natural and Synthetic Endocannabinoids and Their Structure-Activity Relationships"; Current Pharmaceutical Design; 6; 1381-1397; (2000).

Papahatjis et al; "A new ring-forming methodology for the synthesis of conformationally constrained bioactive molecules"; Chemistry Letters, 192; (2001).

Papahatjis et al; "Pharmacophoric requirements for cannabinoid side chains: multiple bond and C1'-substituted delta8-tetrahydrocannabinols"; J. Med. Chem.; 41(7); 1195-1200; (1998).

Pertwee et al; "AM630, a competitive cannabinoid receptor agonist"; Life Sci. 1995, 56(23/24), 1949-1955; XP 000653566.

Pertwee et al; "Pharmacological characterization of three novel cannabinoid receptor agonists in the mouse isolated vas deferens"; Eur. J. Pharmacol. 1995, 284, 241-247; XP-001041044.

Pertwee et al; "Inhibitory effects of certain enantiomeric cannabinoids in the mouse vas deferens and the myenteric plexus preparation of guinea-pig small intestine"; Br. J. Pharmacol.; 105(4); 980-984 (1992). (abstract only).

Pertwee; Pharmacology of cannabinoid CB1 and CB2 receptors; Pharmacol. Ther., vol. 74(2); pp. 129-180; (1997); XP002226467.

Petrov, M.L., Terent'eva, N. A., Potekhin, K.A., Struchkov, Yu. T.; ".alpha.,.beta.-unsaturated thiolates and their analogs in cycloaddition reactions. XVIII. Reaction of (2-phenylethynyl)tellurolates with C-ethoxycarbonyl-N-Phenylnitrilimine"; Zhurnal Organicheskoi Khimii; 29(7); 1372-1378; (1993) (abstract only).

Pinnegan-Ling D, Musty R.; Marinol and phantom limb pain: a case study. *Proc Inv. Cannabinoid Rea. Sec.* (1994):53.

Pinto et al; Cannabinoid Receptor Binding and Agonist Activity of Amides and Esters of Arachidonic Acid; Mol. Pharmacol.; 1994; 46(3); 516-522.

Piomelli D., Beltramo M., Glasnapp S., Lin S.Y., Goutopoulos A., Xiw X-Q., Makriyannis A.; "Structural determinants for recognition and translocation by the anandamide transporter"; Proc. Natl. Acad. Sci. USA; 96; 5802-5807; (1999).

Pitt et al; "The synthesis of Deuterium, carbon-14 and carrier free tritium labellled cannabinoids"; Journal of Labellled Compounds; vol. 11(4); 551-575; 1975; XP002123229.

Porreca F., Mosberg H.I., Hurst R., Hruby V.J., Burks T.F.; "Roles of mu, delta and kappa opiod receptors in spinal and supraspinal mediation of gastrointestinal transit effects and hot-plate analgesia in the mouse"; J. Pharmacol. Exp. Ther.; 230(2); 341-348; (1994). (abstract only).

Quere, L., Boigegrain, R., Jeanjean, F., Gully, D., Evrard, G., Durant, F.; "Structural requirements of non-peptide neurotensin receptor antagonists"; J. Chem Soc., Perkin Trans. 2, (1996); 2639-2646.

Razdan et al; "Drugs derived from cannabinoids. 6. .Synthesis of cyclic analogues of dimethylheptylpyran"; J. Med. Chem.; vol. 19(5); 719-721; 1976 (abstract only).

Razdan et al; "Pharmacological and Behavioral Evaluation of Alkylated Anandamide Analogs"; Life Sci.; 1995; 56(23-24); 2041-2048.

Reggio et al; "Characterization of a region of steric interference at the cannabinoid receptor using the active analog approach"; J. Med. Chem. United States; vol. 36(12); 1761-1771; 1993.

Rhee, M. H.; Vogel, Z.; Barg, J.; Bayewitch, M.; Levy, R.; Hanus, L.; Breuer, A.; and Mechoulam, R.; "Cannabinol Derivatives: Binding to Cannabinoid Receptors and Inhibition of Adenylcyclase"; J. Med. Chem. 1997, 40(20); 3228-3233.

Rice AS. Cannabinoids and pain. Curr Opin Investig Drugs. Mar. 2001;2(3):399-414. (abstract only).

Richardson JD, Aanonsen I, Hargreaves KM; "Antihyperalgesic effects of a spinal cannabinoids"; Eur. J. Pharmacol. (1998) 346:145-153.

Richardson JD, Kilo S. Hargreaves KM; "Cannabinoids reduce dryperalgesia and inflammation via interaction with peripheral CB1 receptors"; Pain (1998) 75:111-119.

Rinaldi-Carmona et al; "Biochemical and pharmacological characterization of SR141716A, the first potent and selective brain cannabinoid receptor antagonist"; Life Sci.; vol. 56(23/24); 1941-1947 (1995).

Rinaldi-Carmona et al; "SR141716A, a potent and selective antagonist of the brain cannabinoid receptor"; FEBS Lett.; 350; 240-244; (1994).

Rompp Chemie Lexikon; Falbe and Regitz; "band 1-A-C1, 8"; Aufl, Thieme Verlag; Stuttgart, S 569-570; 1989.

Santus, Maria; "Studies on thioamides and their derivatives. IX. Synthesis of the derivatives of 1,2,4,5-tetrazine"; Acta Polonae Pharmaceutica; 50(2-3); 183-188; 1993 (abstract only).

Schatz AR et al; "Cannabinoid receptors CB1 and CB2: a characterization of expression and adenylate cyclase modulation within the immune system"; Toxicol Appl Pharmacol. Feb. 1997; 142(2):278-87.

Schuel, H., Burkman, L.J., Picone, R.P., Bo, T., Makriyannis, A., Cannabinoid receptors in human sperm. *Mol. Biol. Cell.*, (1997) (8), 325a.

Serdarevich B., Caroll K.K., "Synthesis and characterization of 1- and 2-monoglycerides of anteiso fatty acids"; J. Lipid Res.; 7; 277-284; (1966).

Shawali, A.S., Albar, H.A.; "Kinetics and mechanism of dehydrochlorination of N-aryl-C-ethoxycarbonyl formohydrazidoyl chlorides"; Canadian Journal Of Chemistry; 64(5); 871-875; 1986 (abstract only).

Shen M. Thayer SA: Cannabinoid receptor agonists protect cultured rat hippocampal neurons from excitotoxicity. Mol. Pharmacol (1996) 54:459-462.

Sheskin, T. et al; Structural Requirements for Binding of Anandamide Type Compounds to the Brain Cannabinoid Receptor; J. Med. Chem.; 1997; 40; 659-667.

Shim et al; "Three-dimensional quantitative structure-activity relationship study of the cannabimimetic (aminoalkyl)indoles using comparative molecular field analysis"; J. Med. Chem.; 1998, 41(23); 4521-4532; XP-002212407.

Shim et al; "Unified pharmacophoric model for cannabinoids and aminoalkylindoles derived from molecular superimposition of CB1 cannabinoid receptor agonists CP55244 and WIN55212-2"; ACS Symposium series, 1999 719 (rational drug design), 165-184; XP-001095771.

Showalter et al; "Evaluation of binding in a transfected cell line expressing a peripheral cannabinoid receptor (CB2): identification of cannabinoid receptor subtype selective ligands"; J. Pharmacol. Exp. Ther., 1996 278(3) 989-999; XP-001097918.

Simiand J, Keane M, Keane PE, Soubrie P: SR 141716, A CB1 cannabinoid receptor antagonist, selectively reduces sweet food intake in marmoset. Behav. Pharmacol (1998) 9:179-181. (abstract only).

Smith P.B. et al; "The pharmacological activity of anandamide, a putative endogenous cannabinoid, in mice"; Journal of Pharmacology and Experimental Therapeutics; vol. 270(1):219-227; 1994.

Terranova J-P, Storme J-J Lafon N. et al; "Improvement of memory in rodents by the selective CB1 cannabinoid receptor antagonist, SR 141716"; Psycho-pharmacol (1996) 126:165-172 (abstract only).

Tetko, I. V. et al; "Volume Learning Algoritm Artificial Neural Networks for 3D QSAR Studies"; J. Med. Chem.; vol. 44, No. 15 (2001) pp. 2411-2420, 2413, 2414 Table 1.

Tius et al; "Conformationally restricted hybrids of CP-55,940 and HHC: Steroeselective synthesis and activity"; Tetrahedron; 50 (9); 2671-2680; (1994) (abstract only).

U.S. Appl. No. 09/600,786, filed Nov. 24, 1999, Makriyannis et al.
U.S. Appl. No. 09/698,071, filed Oct. 30, 2000, Fride et al.
U.S. Appl. No. 10/110,865, filed Oct. 18, 2000, Makriyannis et al.
U.S. Appl. No. 10/110,830, filed Oct. 18, 2000, Makriyannis et al.
U.S. Appl. No. 10/110,812, filed Oct. 18, 2000, Makriyannis et al.
U.S. Appl. No. 10/110,862, filed Oct. 18, 2000, Makriyannis et al.
U.S. Appl. No. 10/111,059, filed Oct. 18, 2000, Makriyannis et al.
U.S. Appl. No. 10/647,544, filed Aug. 25, 2003, Makriyannis et al.

* cited by examiner

INHIBITORS OF THE ANANDAMIDE TRANSPORTER

RELATED APPLICATIONS

This application is a continuation-in-part of U.S. patent application Ser. No. 09/701,989, filed Jan. 29, 2001, which is the National Stage of International Application No. PCT/US99/12900, filed Jun. 9, 1999 which claims the benefit of U.S. Provisional Application No. 60/088,568, filed Jun. 9, 1998, the contents of each of which are herein incorporated by reference.

GOVERNMENT FUNDING

This invention was made with Government support under Contract No. DA 3801 awarded by the National Institute of Drug Abuse. The Government has certain rights in the invention.

BACKGROUND OF THE INVENTION

The marijuana derived cannabinoid $\Delta^9$-tetrahydrocannabinol, $\Delta^9$THC, is known to bind to CB1 receptors in the brain and CB2 receptors in the spleen. Compounds which stimulate those receptors have been shown to induce analgesia and sedation, to cause mood elevation including euphoria and dream states, to control nausea and appetite and to lower intraocular pressure. Cannabinoids have also been shown to suppress the immune system. Thus, compounds which stimulate the receptors, directly or indirectly, are potentially useful in treating glaucoma, preventing tissue rejection in organ transplant patients, controlling nausea in patients undergoing chemotherapy, controlling pain and enhancing the appetite and controlling pain in individuals with AIDS Wasting Syndrome.

In addition to acting at the receptors, cannabinoids also affect cellular membranes, thereby producing undesirable side effects such as drowsiness, impairment of monoamine oxidase function and impairment of non-receptor mediated brain function. The addictive and psychotropic properties of cannabinoids also limit their therapeutic value.

Arachidonyl ethanolamide (anandamide) is an endogenous lipid that binds to and activates cannabinoid receptors and mimics the pharmacological activity of $\Delta^9$THC. In general, anandamide has been found to be somewhat less potent than $\Delta^9$THC. Despite having a rapid onset of action, the magnitude and duration of action of anandamide is relatively short, presumably because of a rapid inactivation process consisting of carrier-mediated transport into cells followed by intra-cellular hydrolysis by a membrane-bound amidohydrolase, anandamide amidase. Thus, inhibitors of anandamide amidase have the effect of indirectly stimulating the receptors by increasing in vivo levels of anandamide. In this connection, attention is directed to Makriyannis et al U.S. Pat. Nos. 5,688,825 and 5,874,459, the disclosures of which are incorporated herein by reference.

Anandamide released by depolarized neurons is believed to be subject to rapid cellular uptake followed by enzymatic degradation. Indeed, rat brain neurons and astrocytes in primary culture avidly take up radioactively labeled anandamide through a mechanism that meets four key criteria of a carrier-mediated transport; temperature dependence, high affinity, substrate selectivity, and saturation. In that other lipids including polyunsaturated fatty acids and prostaglandin $E_2$ ($PGE_2$) enter cells by carrier-mediated transport, it is possible that anandamide uses a similar mechanism. This accumulation may result from the activity of a transmembrane carrier or transporter, which may thus participate in termination of the biological actions of anandamide. This carrier or anandamide transporter is believed to be involved in the inactivation of anandamide. Thus, anandamide released from neurons on depolarization may be rapidly transported back into the cells and subsequently hydrolyzed by an amidase thereby terminating its biological actions. Consequently, the anandamide transporter is a potential therapeutic target for the development of useful medications.

There is considerable interest in understanding the mechanism of anandamide transport and in developing pharmacological agents that selectively interfere with it. Anandamide transport inhibitors may be used as experimental tools to reveal the possible physiological functions of this biologically active lipid. Many of these functions are still elusive despite a growing body of evidence suggesting that the endocannabinoid system is intrinsically active not only in brain and spinal cord, but also in peripheral tissue. Furthermore, anandamide transport inhibitors may offer a rational therapeutic approach to a variety of disease states, including pain, psychomotor disorders, and multiple sclerosis, in which elevation of native anandamide levels may bring about a more favorable response and fewer side effects than direct activation of CB1 receptors by agonist drugs.

SUMMARY OF THE INVENTION

It has now been found that certain analogs of anandamide are potent inhibitors of transport of anandamide across cell membranes. The inventive analogs do not activate the cannabinoid receptors or inhibit anandamide hydrolysis per se but instead prevent anandamide reuptake thereby prolonging the level of the undegraded anandamide. Previously, cannabinoid drugs were targeted toward cannabinoid receptors and amidase enzymes. The anandamide transport inhibitor of the present invention targets activity of the anandamide transporter.

The inhibitors are analogs of anandamide and exhibit the tail, central and head pharmacophore portions represented by Structural Formula I $$X\text{—}Y\text{-}Z. \tag{I}$$

The tail portion X is a fatty acid chain remnant, or an aliphatic hydrocarbon as defined later, or a biphenyl group with an alkyl chain.

The central portion Y is a member selected from the group consisting of —NH—C(O)—, —NH—, —NH—C(O)—NH—, —NH—C(O)—O—, —O—C(O)—NH—, —C(O)—C(O)—NH, —NH—C(O)—C(O)—, —O—C(O)—O—, —C(O)—NH, —O—C(O)—, —O—, —S— and —H. It should be noted that the X and Z portions may be connected to the Y portion at either of the Y portion connecting atoms. Thus, for example, the Y portion —C(O)—NH— will lead to analogs X—C(O)—NH-Z and Z-C(O)—NH—X.

The head portion Z is selected from the group consisting of hydrogen, aryl, substituted aryl, alkyl, alkyl aryl, halogen substituted alkyl aryl, cyclic glycerols and substituted cyclic glycerols, $COCF_3$, C(O)-alcohol, —$(CH_2)_m$—$(C(CH_3)_2)_p$—$(CH_2)_n$-$T_2$-$T_3$, —$(CH_2)_m$—$(CH(CH_3))_q$—$(CH_2)_n$-$T_2$-$T_3$ (where m and n are each independently selected from 0 to 6 integer, p and q are each independently 0 or 1, $T_2$ is optionally present and comprises aryl, a cyclic ring, a bicyclic ring, a tricyclic ring, a heterocyclic ring, a heterobicyclic ring, a heterotricyclic ring, a heteroaromatic ring, 1- or 2-glycerol, 1- or 2-cyclic glycerol, alkyl, alkenyl, alkynyl, $T_3$ comprises H, OH, SH, halogen, C(halogen)$_3$, CH(halogen)$_2$, O-alkyl, N$_3$, CN, NCS, NH$_2$, alkylamino, dialkylamino or a substituent group as defined later).

In variations of the invention the following provisos apply.

When Y is —C(O)—N(H)— and X is the tail remnant of arachidonyl acid, Z excludes 4-hydroxyphenyl.

When Y is —O—C(O)—NH— and X is the tail remnant of arachidonyl acid, Z excludes ethyl, iso-propyl and propyl.

When Y is —NH—C(O)—NH— and X is the tail remnant of arachidonyl acid, Z excludes methyl, iso-propyl, propyl, iso-butyl, CH$_2$CH$_2$F, CH$_2$CH$_2$OH, and CH2CH2OCH3.

When Y is —NH—C(O)—O— and X is the tail remnant of arachidonyl acid, Z excludes ethyl, iso-propyl and CH$_2$CH$_2$F.

When Y is —NH—C(S)—NH— and X is the tail remnant of arachidonyl acid, Z excludes 4-methyl-2-methoxy-phenol, and 4-methyl-2-chloro-phenol.

Some of the inventive analogs described herein, and physiologically acceptable salts thereof, have high potential when administered in therapeutically effective amounts for providing a physiological effect useful to treat pain; peripheral pain; glaucoma; epilepsy; nausea such as associated with cancer chemotherapy; AIDS Wasting Syndrome; cancer; neurodegeneration; neurodegenerative diseases including Multiple Sclerosis, Parkinson's Disease, Huntington's Chorea and Alzheimer's Disease; to enhance appetite; to reduce fertility; to prevent or reduce diseases associated with motor function such as Tourette's syndrome; to provide neuro-protection; to produce peripheral vasodilation and to suppress memory. Thus, another aspect of the invention is the administration of a therapeutically effective amount of an inventive compound, or a physiologically acceptable salt thereof, to an individual or animal to provide a physiological effect.

Some of the novel inhibitors of the present invention, when tested in vitro, inhibit accumulation of anandamide in rat cortical neurons and astrocytes and enhance various effects of anandamide administration both in vitro and in vivo. The vasodepressor responses are significantly potentiated and prolonged by the transport inhibitors. Thus, the inhibitors are believed to be effective drugs for the treatment of cardiovascular diseases and blood pressure disorders.

Beneficially, the inventive compounds would typically not be expected to have the undesirable membrane-related side-effects associated with cannabinoids. In addition, the compounds disclosed herein may be immunosuppressive and can therefore be used to prevent organ rejection in an individual undergoing an organ transplant. The compounds could also be used to treat psychomotor disorders and peripheral hypertension. In all of the above conditions, inhibition of the anandamide transporter and subsequent decrease in anandamide hydrolysis may bring about a more favorable response and fewer side effects than direct activation of CB1 and CB2 receptors by agonist drugs.

The novel inhibitors of anandamide transport disclosed herein also have research uses. For example, they can be used to maintain the level of anandamide in vivo to study the effect of anandamide on individuals and animals. The anandamide transport inhibitors disclosed herein can also be used as an aid in drug design, for example as a control in assays for testing other compounds for their ability to inhibit anandamide transport and to determine the structural and activity requirements of such inhibitors. These results, together with data from initial experiments on the selectivity of radioactively labeled [$^3$H]anandamide uptake by rat brain astrocytes, suggest that the interactions of anandamide with its putative transporter protein are governed by strict structural requirements. These results delineate the broad molecular requisites for this process, thus providing a basis for the design of more potent and selective inhibitors with potential applications to medicine.

Anandamide uptake in neurons and astrocytes has been found to be mediated by a high-affinity, Na$^+$-independent transporter that is selectively inhibited by the inhibitors of the present invention. The structural determinants governing recognition and translocation of substrates by the anandamide transporter have been determined. The secondary amido group interacts favorably with the transporter, but may be replaced with other radicals, suggesting that it may serve as hydrogen acceptor. Putative endogenous cannabinoid esters also serve as a substrate for the transporter. Substrate recognition and translocation require the presence of at least one cis double bond situated at the middle region of the fatty acid hydrocarbon chain or a biphenyl group with an aliphatic chain, indicating a preference for ligands whose hydrophobic tail can adopt a bent U-shaped or hair-pin configuration. Uptake experiments with radioactively labeled substrates favor two or more and preferably four cis nonconjugated double bonds for optimal translocation across the cell membrane, suggesting that substrates are transported in a folded hairpin conformation.

The inventive compounds include any and all possible isomers, stereoisomers and enantiomers. In general, the compositions of the invention may be alternately formulated to comprise, consist of, or consist essentially of, any appropriate components herein disclosed. The compositions of the invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

A better understanding of the invention will be obtained from the following detailed description of the presently preferred, albeit illustrative, embodiments of the invention.

DETAILED DESCRIPTION OF THE INVENTION

Figure 1:
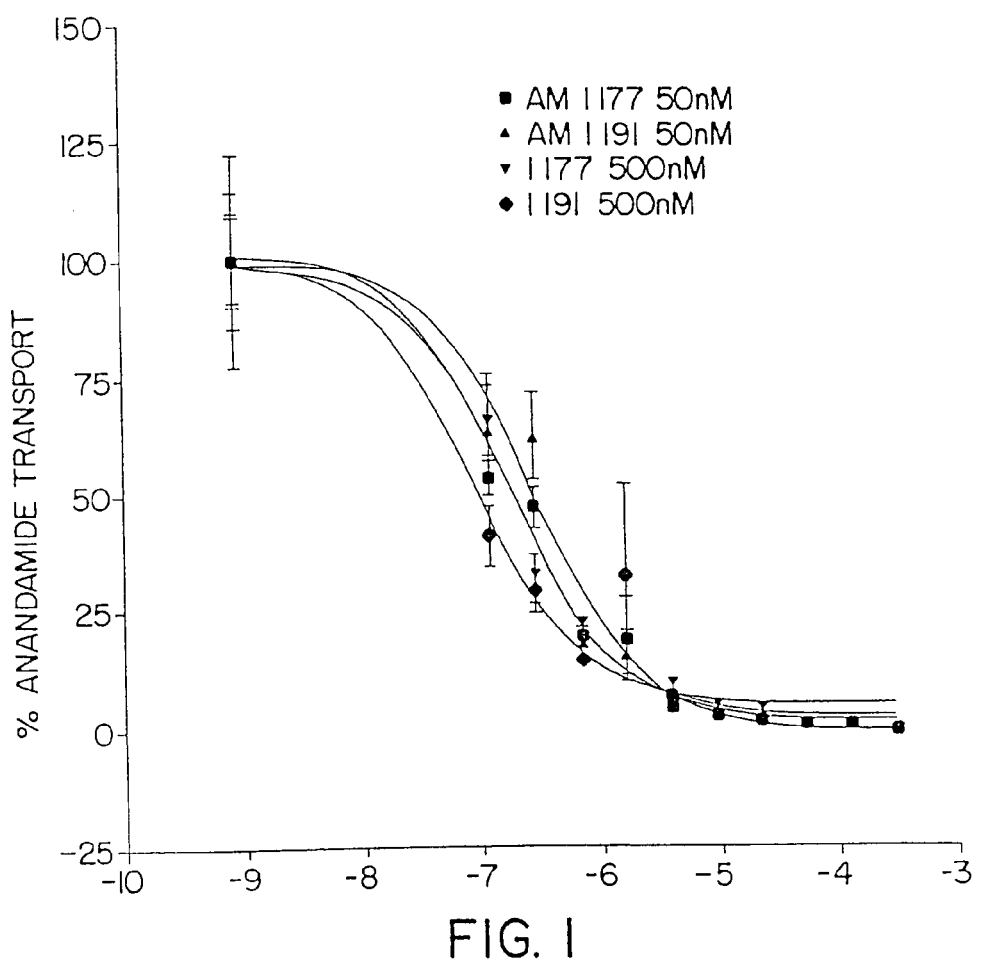
FIG. 1 is a graph showing the translocation of substrate inhibitors of the present invention at different concentration levels.

One embodiment of the present invention is directed to the discovery of a putative anandamide transporter system which has been characterized biochemically and pharmacologically and which can be used as a target for the discovery of novel medications. These would include all compounds that can inhibit the function of this transporter. The invention further includes the pharmacological formula containing an effective amount of the inhibitor while another embodiment is directed to a method of inhibiting anandamide transport in an individual or animal by administering a therapeutically effective amount of the inhibitor and/or physiologically acceptable salts thereof. The inhibition results in increased levels of anandamide in the individual or animal, thereby causing prolonged stimulation of cannabinoid receptors in the individual or animal, e.g., the CB1 receptor in the brain and the CB2 receptor in the spleen. Thus, the present invention involves not only the inhibitor itself but also a method of reducing anandamide transporter activity in an individual or animal. It is to be understood that the present invention may also be used to reduce the activity of transporters not yet discovered for which anandamide and/or a cannabinoid act as an agonist.

In some embodiments the anandamide transport inhibitors of the present invention include amide, reverse amide or carbonyl amine, urea, carbamate and ester analogs of anandamide having the three pharmacophores of the Structural Formula I wherein the tail portion X is a fatty acid hydrophobic carbon chain having one or more nonconjugated cis double bonds in the middle portion of the aliphatic hydrocarbon chain or a biphenyl group having an alkyl or branched alkyl distal moiety of about 1 to about 10 carbon atoms. The biphenyl group is substituted with 1-6 substituents including OH, $CH_3$, halogen, $SCH_3$, $NH_2$, NHCOR, $SO_2NHR$, $NO_2$, $COCF_3$, or a substituent group as defined later. The fatty acid chain may contain four to thirty carbon atoms but preferably the chain length is about 10 to 28 carbon atoms and more preferably contains from about 17 to about 22 carbon atoms. The aliphatic hydrocarbon chain may terminate with an aryl or substituted aryl group. By contrast, analogs with fully saturated chains or with a trans or terminal double bond fail to compete successfully with [$^3$H]anandamide for transport and thus are ineffective as inhibitors. The central pharmacophore Y is selected from the group set forth hereinbefore. However, compounds containing a free carboxylic acid, carboxyethyl and carboxymethyl groups, or a primary alcohol are inactive. The head portion Z is selected from the group set forth hereinbefore.

Exploration of the Y and Z pharmacophores shows that compounds containing primary, secondary and tertiary amido groups as well as hydroxymethyl ester or glycerol ester moieties are capable of competing with [$^3$H]anandamide, but exhibit a wide range of potencies. Structural variations of the head group Z leads to analogs with diverse selectivities for the anandamide transporter. Thus substitution of the terminal hydroxyl with a hydrogen causes a substantial decrease in potency, whereas replacement of the entire hydroxyalkyl moiety with hydrogen yields compounds that are as potent as anandamide. Introduction of a methyl group alpha to the amido nitrogen also leads to active compounds. Some chiral molecules display considerable enantioselective inhibition of [$^3$H]anandamide transport. The (S) enantiomer is approximately four times more potent than its (R) isomer.

One striking structure-activity correlation was observed with analogs having hydroxyphenyl radicals at the head group. Use of the hydroxyphenyl group leads to relatively potent uptake inhibitors, with the 4-hydroxyphenyl analog being distinctly the most successful.

Unless otherwise specifically defined, "acyl" refers to the general formula —C(O)alkyl.

Unless otherwise specifically defined, "acyloxy" refers to the general formula —O-acyl.

Unless otherwise specifically defined, "alcohol" refers to the general formula alkyl-OH and includes primary, secondary and tertiary variations.

Unless otherwise specifically defined, "alkyl" or "lower alkyl" refers to a linear, branched or cyclic alkyl group having from 1 to about 16 carbon atoms, and advantageously about 1 to about 6 carbon atoms, including, for example, methyl, ethyl, propyl, butyl, hexyl, octyl, isopropyl, isobutyl, tert-butyl, cyclopropyl, cyclohexyl, cyclooctyl, vinyl and allyl. The alkyl group can be saturated or unsaturated. Unless otherwise specifically limited, an alkyl group can be unsubstituted, singly substituted or, if possible, multiply substituted, with substituent groups in any possible position. Unless otherwise specifically limited, a cyclic alkyl group includes monocyclic, bicyclic, tricyclic and polycyclic rings, for example norbornyl, adamantyl and related terpenes.

Unless otherwise specifically defined an aliphatic hydrocarbon includes, unless otherwise stated, one or more polyalkylene groups connected by one or more cis-alkenyl linkages such that the total number of methylene carbon atoms is within the ranges set forth herein. The structure of preferred aliphatic hydrocarbons comprising the tail portion X have the formula II

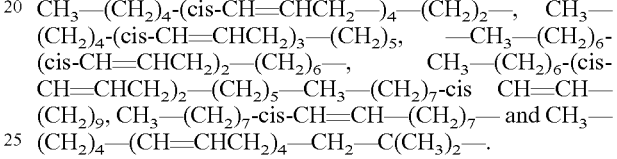
(II)

wherein each of $R_0$ to $R_3$ is independently selected from the groups consisting of hydrogen and lower alkyl groups, however the chain's terminal $C(R_3)_3$ may include phenyl and biphenyl groups that are unsubstituted or substituted with a member selected from the group consisting of hydroxyl, halogen, —$NO_2$, —$NH_2$, —$SCH_3$, —$CH_3$, —$COCF_3$, and —$OCH_3$ or a substituent group as defined later, and a and c are each independently selected integers 0 to 10 and b is an integer from 1 to 6. Specific examples include $CH_3$—$(CH_2)_4$-(cis-CH=$CHCH_2$—)$_4$—$(CH_2)_2$—, $CH_3$—$(CH_2)_4$-(cis-CH=$CHCH_2$)$_3$—$(CH_2)_5$, —$CH_3$—$(CH_2)_6$-(cis-CH=$CHCH_2$)$_2$—$(CH_2)_6$—, $CH_3$—$(CH_2)_6$-(cis-CH=$CHCH_2$)$_2$—$(CH_2)_5$—$CH_3$—$(CH_2)_7$-cis CH=CH—$(CH_2)_9$, $CH_3$—$(CH_2)_7$-cis-CH=CH—$(CH_2)_7$— and $CH_3$—$(CH_2)_4$—(CH=$CHCH_2$)$_4$—$CH_2$—$C(CH_3)_2$—.

The aliphatic hydrocarbon also includes long chain hydrocarbons possessing 8 to 22 carbons and having zero to six of double bonds and optionally substituted in any possible position with lower-alkyl, di-lower-alkyl, cycloalkyl or heterocycloalkyl groups; of which the multiple double bonds can be conjugated or unconjugated. The aliphatic hydrocarbon backbone chain may be interrupted with, or otherwise include, methylene, $(CH_3)_2C$, O, NH, N-alkyl, cyclic alkyl groups, heterocyclic groups and aryl groups.

Unless otherwise specifically defined, "alkoxy" refers to the general formula —O-alkyl.

Unless otherwise specifically defined, "alkylmercapto" refers to the general formula —S-alkyl.

Unless otherwise specifically defined, "alkylamino" refers to the general formula —(NH)-alkyl.

Unless otherwise specifically defined, "di-alkylamino" refers to the general formula —N(alkyl)$_2$. Unless otherwise specifically limited di-alkylamino includes cyclic amine compounds such as piperidine and morpholine.

Unless otherwise specifically defined, an aromatic ring is an unsaturated ring structure having about 5 to about 7 ring members and including only carbon as ring atoms. The aromatic ring structure can be unsubstituted, singly substituted or, if possible, multiply substituted, with substituent groups in any possible position.

Unless otherwise specifically defined, "aryl" refers to an aromatic ring system that includes only carbon as ring atoms, for example phenyl, biphenyl, 1-naphthyl or 2-naphthyl. The aryl group can be unsubstituted, singly substituted or, if possible, multiply substituted, with substituent groups in any possible position.

Unless otherwise specifically defined, "aroyl" refers to the general formula —C(=O)-aryl.

Unless otherwise specifically defined, a bicyclic ring structure comprises 2 fused or bridged rings that include only carbon as ring atoms. The bicyclic ring structure can be saturated or unsaturated. The bicyclic ring structure can be unsubstituted, singly substituted or, if possible, multiply substituted, with substituent groups in any possible position. The individual rings may or may not be of the same type. Examples of bicyclic ring structures include, Dimethyl-bicyclo[3,1,1]heptane, bicyclo[2,2,1]heptadiene, decahydronaphthalene and bicyclooctane.

Unless otherwise specifically defined, a carbocyclic ring is a non-aromatic ring structure, saturated or unsaturated, having about 3 to about 8 ring members that includes only carbon as ring atoms, for example, cyclohexadiene or cyclohexane. The carbocyclic ring can be unsubstituted, singly substituted or, if possible, multiply substituted, with substituent groups in any possible position.

Unless otherwise specifically defined, a cyclic glycerol includes members wherein 2 of the 3 hydroxy groups are tied to form a 5 to 8 member ring and the third hydroxyl group is substituted, for example in the form of an ester or an ether. The cyclic glycerol ring will typically, but not always, be saturated. The cyclic glycerol may be substituted in any possible position by one or more substituent groups. Examples of cyclic glycerols include

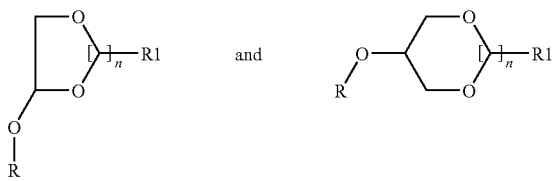

wherein n is an integer selected from 1 to 3.

Unless otherwise specifically defined, "halogen" refers to an atom selected from fluorine, chlorine, bromine and iodine.

Unless otherwise specifically defined, a heteroaromatic ring is an unsaturated ring structure having about 5 to about 8 ring members that has carbon atoms and one or more heteroatoms, including oxygen, nitrogen and/or sulfur, as ring atoms, for example, pyridine, furan, quinoline, and their derivatives. The heteroaromatic ring can be unsubstituted, singly substituted or, if possible, multiply substituted, with substituent groups in any possible position.

Unless otherwise specifically defined, a heterobicyclic ring structure comprises 2 fused or bridged rings that include carbon and one or more heteroatoms, including oxygen, nitrogen and/or sulfur, as ring atoms. The heterobicyclic ring structure is saturated or unsaturated. The heterobicyclic ring can be unsubstituted, singly substituted or, if possible, multiply substituted, with substituent groups in any possible position. The individual rings may or may not be of the same type. Examples of heterobicyclic ring structures include tropane, quinuclidine and tetrahydro-benzofuran.

Unless otherwise specifically defined, a heterocyclic ring is a saturated or unsaturated ring structure having about 3 to about 8 ring members that has carbon atoms and one or more heteroatoms, including oxygen, nitrogen and/or sulfur, as ring atoms, for example, piperidine, morpholine, piperazine, pyrrolidine, thiomorpholine, tetrahydropyridine, and their derivatives. The heterocyclic ring can be unsubstituted, singly substituted or, if possible, multiply substituted, with substituent groups in any possible position.

Unless otherwise specifically defined, a heterotricyclic ring structure comprises 3 rings that may be fused, bridged or both fused and bridged, and that include carbon and one or more heteroatoms, including oxygen, nitrogen and/or sulfur, as ring atoms. The heterotricyclic ring structure can be saturated or unsaturated. The heterotricyclic ring structure can be unsubstituted, singly substituted or, if possible, multiply substituted, with substituent groups in any possible position. The individual rings may or may not be of the same type. Examples of heterotricyclic ring structures include 2, 4, 10-trioxaadamantane, tetradecahydro-phenanthroline.

Unless otherwise specifically defined, a heteropolycyclic ring structure comprises more than 3 rings that may be fused, bridged or both fused and that include carbon and one or more heteroatoms, including oxygen, nitrogen and/or sulfur, as ring atoms. The heteropolycyclic ring structure can be saturated or unsaturated. The heteropolycyclic ring structure can be unsubstituted, singly substituted or, if possible, multiply substituted, with substituent groups in any possible position. The individual rings may or may not be of the same type. Examples of heteropolycyclic ring structures include azaadamantine, 5-norbornene-2,3-dicarboximide.

Unless otherwise specifically defined, the term "phenacyl" refers to the general formula -phenyl-acyl.

Unless otherwise specifically defined, a polycyclic ring structure comprises more than 3 rings that may be fused, bridged or both fused and bridged, and that includes carbon as ring atoms. The polycyclic ring structure can be saturated or unsaturated.

The polycyclic ring structure can be unsubstituted, singly substituted or, if possible, multiply substituted, with substituent groups in any possible position. The individual rings may or may not be of the same type. Examples of polycyclic ring structures include adamantine, bicyclooctane, norbornane and bicyclononanes.

Unless otherwise specifically defined, a spirocycle refers to a ring system wherein a single atom is the only common member of two rings. A spirocycle can comprise a saturated carbocyclic ring comprising about 3 to about 8 ring members, a heterocyclic ring comprising about 3 to about 8 ring atoms wherein up to about 3 ring atoms may be N, S, or O or a combination thereof.

Unless otherwise specifically defined, a tricyclic ring structure comprises 3 rings that may be fused, bridged or both fused and bridged, and that includes carbon as ring atoms. The tricyclic ring structure can be saturated or unsaturated. The tricyclic ring structure can be unsubstituted, singly substituted or, if possible, multiply substituted, with substituent groups in any possible position and may be substituted or unsubstituted. The individual rings may or may not be of the same type. Examples of tricyclic ring structures include fluorene and anthracene.

Unless otherwise specifically limited the term substituted means substituted by a below-described substituent group in any possible position. Substituent groups for the above moieties useful in the invention are those groups that do not significantly diminish the biological activity of the inventive compound. Unless otherwise specifically limited a substituent group or a substituent group that does not significantly diminish the biological activity of the inventive compound includes, for example, H, halogen, $N_3$, NCS, CN, $NO_2$, $NX_1X_2$, $OX_3$, $C(X_3)_3$, OAc, O-acyl, O-aroyl, NH-acyl, NH-aroyl, NHCOalkyl, CHO, C(halogen)$_3$, $COOX_3$, $COCF_3$, $SO_3H$, $PO_3H_2$, $SO_2NX_1X_2$, $CONX_1X_2$, alkyl, alcohol, alkoxy, alkylmercapto, alkylamino, di-alkylamino, sulfonamide or thioalkoxy wherein $X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and X2 together comprise part of an imide ring having about 5 to about 6 members and $X_3$ comprises H, alkyl, loweralkylhydroxy, or alkyl-$NX_1X_2$. Unless otherwise specifically limited, a substituent group may be in any possible position.

Procedures for Synthesizing these Materials Are as Follows:

Arachidonyl alcohol: To a magnetically stirred solution of 0.5 ml (0.5 mmol) of LiAlH$_4$ in Et$_2$O, 100 mg (0.314 mmol) of arachidonic acid methyl ester in 2 mL of Et$_2$O was added dropwise at 0° C. The reaction mixture was stirred for 1 h and then quenched by addition of 1 mL of EtOAC. 2 mL of saturated NH₄Cl solution was added and the organic layer was separated, dried with MgSO₄, filtered and evaporated. Chromatography on silica gel (eluents: CH₂Cl₂/petroleum ether up to 70% CH₂Cl₂), evaporation, followed by Millipore filtration of a CH₂Cl₂ solution of the product gave 99.3 mg (0.292 mmol, 93% yield) of arachidonyl alcohol as a colorless oil: TLC (CHCl₃) R$_f$ 0.28; ¹H NMR (200 MHz, CDCl₃) δ 5.37 (m, 8 H), 3.61 (t, 2 H, J=6 Hz), 2.79 (m, 6H), 2.08 (m, 4 H), 1.66-1.17 (m, 8 H), 0.92 (t, 3 H, J=7 Hz).

Arachidonyl azide: To a magnetically stirred solution of 50 mg (0.17 mmol) of arachidonyl alcohol in 1 mL of pyridine 29.2 mg. (0.255 mmol) of mesyl chloride was added at 0° C. After stirring for 5 h, the reaction mixture was poured into 2 mL of iced water and extracted with Et₂O (2×4 mL). The ethereal layers were combined and washed with 1 N H₂SO₄, NaHCO₃, and evaporated in vacuo to dryness. The mesylate was not purified and it was directly converted to the corresponding azide: it was dissolved first in 2 ml DMF and then 4 ml of solution of 6.5 mg. (0.85 mmol) NaN₃ in DMF was added at room temperature. The reaction mixture was heated at 90° C. for 24 h. After the reaction mixture was cooled down to room temperature the inorganic material was filtered off and the filtrated was poured into 1 mL of iced H₂O and then extracted with Et₂O (2×6 mL). The ethereal layers were combined, dried, filtered, and evaporated in vacuo to dryness. Silica gel chromatography (eluent: petroleum ether), evaporation, followed by Millipore filtration of a CH₂Cl₂ solution of the product gave 39 mg (0.12 mmol, 73% yield) of arachidonyl axide as a colorless oil: ¹H NMR (200 MHz, CDCl₃) δ 5.38 (m, 8 H), 3.27 (t, 2 H, J=6 Hz), 2.81 (m, 6H), 2.11-2.01 (m, 4), 162 m, 2 H), 1.48-1.25 (m, 6 H), 0.89 (t, 3 H, J=7 Hz).

Arachidonylamine: To a magnetically stirred solution of 132 mg (0.43 mmol) of arachidonyl azide in 3 mL of Et₂O, 4 mL of a 1.0 M LAH solution in THF (4.0 mmol) was added dropwise at room temperature. The reaction mixture was refluxed for 3 h and then it was cooled to ambient temperature. 210 mg (5 mmol) of NaF was added and the reaction was quenched with wet Et₂O. The white mixture was filtered and the solvent was evaporated to dryness. Silica gel chromatography (eluents: CH₂Cl₂/MeOP-up to 50% MeOH), evaporation of solvent, followed by Millipore filtration of a CH₂Cl₂ solution of the product then gave 78.9 mg (0.28 mmol, 64% yield) of arachidonyl-amine as a colorless oil. TLC (EtOAc/CH₂Cl₂ (20:80)) R$_f$ 0.33; ¹H NMR (200 MHz, CDCl₃) δ 5.38 (m, 8 H), 2.82 (m, 6 H), 2.70 (t, 2 H, J=6.6 Hz), 2.08 (m, 4 H), 1.40 (m, 4 H), 1.26 (m, 6 H), 0.89 (t, 3 H, J=6.4 Hz).

Typical procedure for synthesis of AM 1177, AM 1172 and AM 1191 is as follow: To a suspension of arachidonyl amine or arachidonyl acid (1 mmol) and 1-[3-(dimethylamino)propyl]-3-ethylcarbodimide hydrochloride (EDCl) (1.2 mmol) in 5 mL THF was added a solution of 1.1 mmol of corresponding acid, or alcohol (Stekar, J., et. al. Angew. Chem.; GE; 1995, 107: 195-197.) in 1 mL THF at room temperature followed by addition of a solution of dimethylaminopyridine (DMAP) (1.1 mmol) in 1 mL THF. The stirring was continued for another 6 h. The THF was removed in vacuo, and the residue was re-dissolved in Et₂O. The resulting solution was washed wash with water, 1N HCl and brine, respectively, dried over Na₂SO₄. The solvent was removed in vacuo, and residue was purified by column chromatograph on silica gel to afford pure AM 1177 AM 1172 and AM 1191 (0.6-0.8 mmol, 60-80% yield) as oil.

Arachidonylamine-3'-(hydroxy)-propionate: To a magnetically stirred solution of 48 mg (0.17 mmol) of arachidonyl-amine in 2 mL of CH₂Cl₂, 58 µl (0.17 mmol) of a 2.0 M solution of (CH₃)₃Al in of hexane were added at room temperature. The mixture was stirred for 20 min and then 12.24 mg (0.17 mmol) of β-propiolactone was added dropwise. The reaction mixture was refluxed for 6 h, quenched with 1N HCl and extracted with methyl chloride. The product was purified with silica gel column chromatography (eluents with CH₂Cl₂/EtOAc, up to 80% EtOAc. Evaporation of the solvent, followed by Millipore filtration of a CH₂Cl₂ solution of the product gave 51 mg (0.14 mmol, 83% yield) of arachidonyl-amine-3'-(hydroxy)-propionate as a colorless oil; TLC (EtOAc) R$_f$ 0.26; ¹H NMR (200 MHz, CDCl₃) δ 5.35 (m, 8 H), 3.85 (q, 2 H, J=5.4 Hz), 3.25 (q, 2 H, J=5.4 Hz), 2.84 (m, 6 H), 2.66 (t, 2 H, J=6.8 Hz), 2.05 (m, 4 H), 1.57 (m, 2 H), 1.35 (m, 6 H) 0.89 (t, 3, H, J=6.5 Hz); Anal. C, H, N.

Arachidonyl-amine-trifluoroacetate: To a magnetically stirred solution of 69 mg (0.6 mmol) of trifluoroacetic acid, in 2 ml of dry methylene chloride, at 0° C., 0.046 ml (0.6 mmol) of dry DMF was added and then 0.3 ml (0.6 mmol) of 2.0 M solution of oxalyl chloride in methylene chloride, dropwise. The reaction mixture was stirred for 20 min and then a solution of 172 mg (0.6 mmol) of arachidonyl amine in 2 ml of methylene chloride was added and the reaction was stirred for 2 hrs at ambient temperature. The product was purified with silica gel column chromatography (eluents: petroleum ether/ethyl acetate, up to 50% ethyl acetate). Evaporation of the solvent, followed by Millipore filtration of a CH₂Cl₂ solution of the product gave 153 mg (0.4 mmol, 67% yield) of arachidonyl-amine-trifluoroacetate as a colorless oil.

Preparation of Compound 1-12:

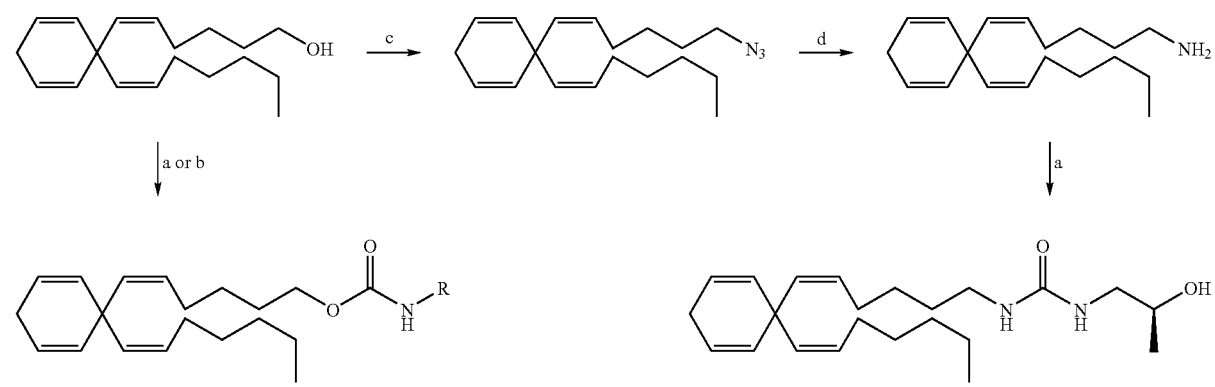

a. CO(imidazole)₂, amines, THF, 70-90%; b. diphosgene, Et₃N, THF, amines, 85-90%; c. Zn(N₃)₂·2Py, DIAD, PPh₃, toluene, 0° C.-r.t., 85%; d. H₄LiAl, Et₂O, 84%

Compound 1-8 and 12

Method A: To a suspension of CO(imidazole)₂ (1.5 mmol) in 3 mL of anhydrous THF was added a solution of arachidonyl alcohol or arachidonyl amine (1 mmol) in 1 mL THF at 0° C. Stirring was continued for another 2 h at ambient temperature. Then, the reaction mixture was cooled to 0° C. again, and the respective amine (2 mmol) was added and stirred for overnight. THF was removed in vacuo, and the residue was diluted with Et₂O. The heterogeneous mixture was filtered with a pad of Celite, and filtrate was washed with 2N HCl, saturated NaHCO₃ and brine, respectively, dried over Na₂SO₄. The solvent was removed in vacuo, and residue was chromatographed on silica gel to afford pure compounds 1-8 and 12 (0.7-0.9 mmol, 70-90% yield) as oil.

Compound 9-11:

Method B: To a suspension of arachidonyl alcohol (1 mmol) and activated carbon (0.1 mmol) in 3 mL of anhydrous THF was added diphosgene (0.75 mmol) at 0° C. Stirring was continued for another 2 h at 0° C. Then, a solution of respective amine (2 mmol) Et₃N (6 mmol) in 1 mL of THF was added to above reaction mixture and stirring was continued for overnight. It was diluted with Et₂O, and heterogeneous mixture was filtered with a pad of Celite. The filtrate was washed with water and brine, dried over Na₂SO₄ and concentrated in vacuo. The residue was chromatographed to give pure compounds 9-11 (0.82-0.90 mmol, 82-90% yield) as oil.

Preparation of Compound 13-15:

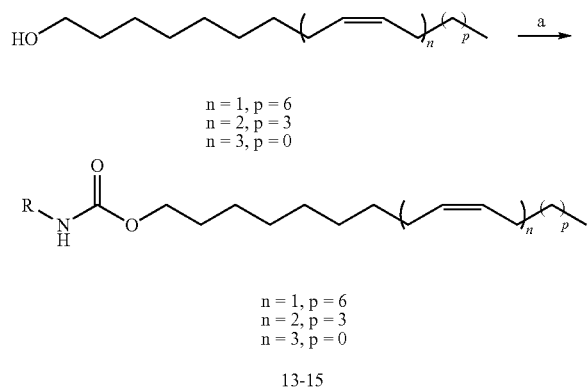

13-15
a. CO(imidazole)₂, amines, THF, 75-87%

Compound 13-15:

Preparation of 13-15 can be fulfilled from corresponding commercially available alcohols following the procedure of preparation of compounds 1-8.

Preparation of Compound 16:

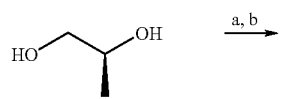

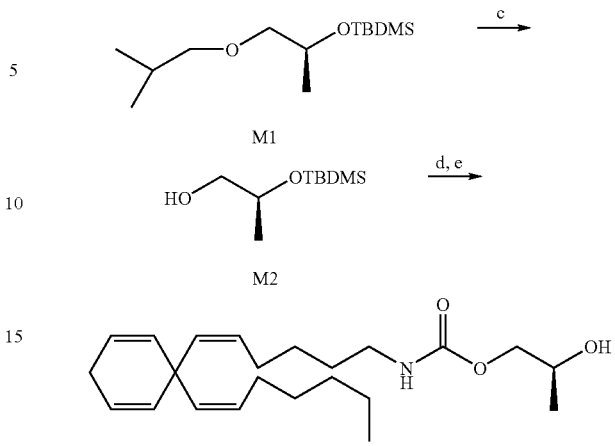

Compound M1:

To a solution of (S)-1,2-propandiol (5 mmol) in 5 mL of anhydrous CH₂Cl₂ were added 2-methyl-1-butene (5.5 mmol) and BF₃ etherate (0.5 mmol) at room temperature. The stirring was continued for another 24 h. The solvent was removed by vacuum, and the residue was purified by chromatograph on silica gel to afford intermediate (4 mmol, 80% yield) as oil. Then, to a suspension of this intermediate and imidazole (6 mmol) in 6 mL of anhydrous THF was added 4.8 mL of TBDMSCl (1M in THF) at 0° C. The solvent was removed by vacuum, and the residue was re-dissolved in Et₂O. The heterogeneous mixture was filtered over a pad of Celite. The filtrate was washed with 1N HCl, water and brine, dried over Na₂SO₄ and concentrated in vacuo. The residue was chromatographed to give pure M1 (0.34 mmol, 85% yield) as oil.

Compound M2:

To a solution of M1 (3 mmol) in 3 mL of anhydrous CH₂Cl₂ was added TBDMSOTf (0.3 mmol) at room temperature, and the resulting solution was stirred for 24 hours. Saturated NaHCO₃ was then added and the solution extracted with AcOEt. Combined organic layers were dried over Na₂SO₄ and concentrated in vacuo. The crude product was purified by chromatograph on silica gel to afford M2 (1.8 mmol, 60% yield) as oil.

Compound 16:

The 16 can be made in two steps. The first one is coupling, which can be fulfilled by following the similar procures of preparation of 1-8 in 83% yield. The second step is deprotection by TBAF. To a solution of coupling product (1 mmol) in 2 mL of THF was added 1.2 mL of TBAF (1M in THF) at room temperature. The stirring was continued for another 1.5 h. Then, the THF was removed in vacuum, and the resulting mixture was dissolved in Et₂O. The resulting solution was washed by water and brine, dried over Na₂SO₄ and concentrated in vacuum. The crude product was purified by chromatograph on silica gel to afford 16 (0.8 mmol, 80% yield) as oil.

Preparation of Compound 17-25

Typical procedure for synthesis of compounds 17-25 is as following:

To a magnetically stirred solution of arachidonic acid (1 mmol) and DMF (0.1 mmol) in 5 mL of methylene chloride in a 25-mL three-neck flask at 0° C. was added oxalyl chloride (2 mmol) in a dropwise manner. The reaction mixture was stirred further at 0° C. for an additional hour. Then a solution of corresponding amine (10 mmol) in 5 mL of THF was added. Stirring was continued further for 15 min. The reaction mixture was diluted with 30 mL of $CH_2Cl_2$ and washed successively with 30 mL of 10% of aqueous HCl, 30 mL of 10% aqueous NaOH, and water. The organic phase was separated, dried ($MgSO_4$), and evaporated in vacuo to give a yellowish oily residue. Chromatography on silica gel afforded final compounds 17-25 (0.6-0.9 mmol, 60-90% yield) as oil.

The Transporter.

In order to properly evaluate the effectiveness of inhibitors of anandamide transport, it was necessary to establish the identity and character of the carrier-mediated transporter. The accumulation of radioactively labeled exogenous [$^3$H]anandamide by neurons and astrocytes fulfills several criteria of a carrier-mediated transport. It is a rapid process that reaches 50% of its maximum within about four minutes. Furthermore, [$^3$H]anandamide accumulation is temperature dependent and saturable. Kinetic analyses reveals that accumulation in neurons can be represented by two components of differing affinities (lower affinity: Michaelis constant, $K_m$=1.2 µM, maximum accumulation rate, $V_{max}$=90.9 pmol/min per milligram of protein; higher affinity: $K_m$=0.032 µM, $V_{max}$=5.9 pmol/min per milligram of protein). The higher affinity component may reflect a binding site, however, as it is displaced by the cannabinoid receptor antagonist, SR-141716-A (100 nM). In astrocytes, [$^3$H]anandamide accumulation is represented by a single high-affinity component ($K_m$=0.32 µM, $V_{max}$=171 pmol/min per milligram of protein). Such apparent $K_m$ values are similar to those of known neurotransmitter uptake systems and are suggestive therefore of high-affinity carrier-mediated transport.

To characterize further this putative anandamide transporter, cortical astrocytes in culture were employed. As expected from a selective process, the temperature-sensitive component of [$^3$H]anandamide accumulation was prevented by nonradioactive anandamide, but not by palmitoyl ethanolamide, arachidonate, prostanoids, or leukotrienes. Replacement of extracellular sodium ion with N-dimethylglocosamine or choline had no effect suggesting that accumulation is mediated by a $Na^+$-independent mechanism which has been observed for other lipids. Moreover, inhibition of fatty acid amide hydrolase (FAAH) activity indicates that an anandamide hydrolysis does not provide the driving force for anandamide transport into astrocytes within the time frame of the experiment. Finally, the cannabinoid receptor agonist WIN-55212-2 (1 µM) and antagonist SR-141716-A (10 µM) also had no effect, suggesting that receptor internalization was not involved.

A primary criterion for defining carrier-mediated transport is pharmacological inhibition. To identify inhibitors of anandamide transport, examination was made of various components that prevent the cellular uptake of other lipids such as fatty acids, phospholipids or bromcresol green. Among the compounds tested, only bromcresol green interfered with inanimate transport, albeit with limited potency and partial efficacy, bromcresol green inhibited [$^3$H]anandamide accumulation with an $IC_{50}$ (concentration needed to produce half-maximal inhibition) of 4 µM in neurons and 12 µM in astrocytes and acted noncompetitively. Moreover, bromcresol green had no significant effect on the binding of [$^3$H]WIN-55212-2 to rat cerebral membranes, on FAAH activity in brain microsomes and on uptake of [$^3$H]arachidonate or [$^3$H]ethanolamine in astrocytes.

The bromcresol green, which blocks $PGE_2$ transport, raised the question of whether anandamide accumulation occurred by means of a $PGE_2$ carrier. That this is not the case was shown by the lack of [$^3$H]$PGE_2$ accumulation in neurons or astrocytes and by the inability of $PGE_2$ to interfere with [$^3$H]anandamide accumulation. Previous results indicating that expression of $PGE_2$ transporter mRNA in brain tissue is not detectable further support this conclusion.

[$^3$H] Anandamide Competition Assay Using a High Throughput Method.

Human CCF-STTG1 astrocytoma cells (American Type Culture Collection) were grown in RPMI 1640 culture medium containing 10% FBS and 1 mM glutamine. Cells were seeded at a density of $2 \times 10^5$/well=$6 \times 10^5$/cm$^2$ and used at confluence (5 days post seeding). For standard competition assays, confluent cells grown in 96-well view plates were rinsed and preincubated for 10 min. at 37° C. in Hanks Balanced Salt Solution (HBSS) supplemented to contain 138 mM NaCl, 5 mM KCl, 1.26 mM MgSO4, 2.5 mM $CaCl_2$-$2H_2O$, 1 mM phosphates, 4 mM $NaHCO_3$, 10 mM glucose, 10 mM Hepes with 0.1% DMSO or 0.1% DMSO plus test compounds at their final concentrations (0.1-100 µM). Briefly, plates of cells were washed 3× with 100 ul with HBSS with 0.1% DMSO with a Multiwash Plus (Molecular Device) plate washer. Washed plates were placed into a plate warmer with an air:carbon dioxide mixture of 95:5.

A silanized 96 well plate was prepared as a mother plate for treating the cells. For each test compound a dilution sheet was generated to encompass a range of concentrations around a predicted $IC_{50}$ of 500 nM.

To the motherplate, 150 ul of a 2× dilution of test compound was added to two rows columns 1-12 or the 96 well mother plate. Add 150 ul of HBSS with 0.1% DMSO to each well of one of ROW A (label this row as pretreatment). To row B add 150 ul per well of [$^3$H]anandamide 100 or 1000 nM and label this row as treatment. This results in a 1× concentration of test compounds and a 50 or 500 nM concentration final concentration of anandamide.

Take the mother plate and set the electrapipette to fill 225 ul and dispense 50 ul of the pretreatment to the appropriate wells. Next decant the 96 well plate to remove the 100 ul of wash buffer. Add 50 ul per well for an n=4 columnwise down for rows a-d for test compound number 1. Then add 50 ul of compound 2 per well for 4 columnwise transfers to rows e-h. Place the plates back into the plate warmer/incubator.

After the 10 minute preincubation period, decant the plates. With the mother plate, set the electrapipette to fill 225 ul and dispense 50 ul of the treatment to the appropriate wells. Place the plate back into the plate warmer for 4 minutes. Then decant the plate into the hot sink and immediately aspirate the incubation media using the Filtermate 196 Cell Harvester (Packard Instruments, Meriden, Conn.), followed by rinsing the cells 6× with ice-cold HBSS containing 0.1% fatty acid free bovine serum albumin (Sigma).

Reactions were stopped by removing the incubation media and rinsing the cells three times with 0.1 ml of ice-cold HBSS containing 0.1% fatty acid-free BSA (Sigma). A final wash of the plate in HBSS was performed to remove any traces of albumin for the following protein analysis.

Cells were then solubilized by the addition of 50 ul/well of 1.2N NaOH/0.1% Triton X-100 and shaken on a plate shaker for 10 minutes. Aliquots of 15 ul were removed for protein analysis using the Biorad DC protein kit. To the remaining cell extracts in the viewplates, 215 ul of Microscint-20 were added and radioactive material was measured by liquid scintillation counting. Preliminary analyses carried out by TLC demonstrated that >95% of this radioactive material was non-metabolized [$^3$H]anandamide, suggesting that our astrocytoma cell preparation contains no significant anandamide amidohydrolase activity.

Some of the inhibitors have been identified as competitive since they are recognized as substrates by the transporter and will undergo membrane translocation.

Figure 2:
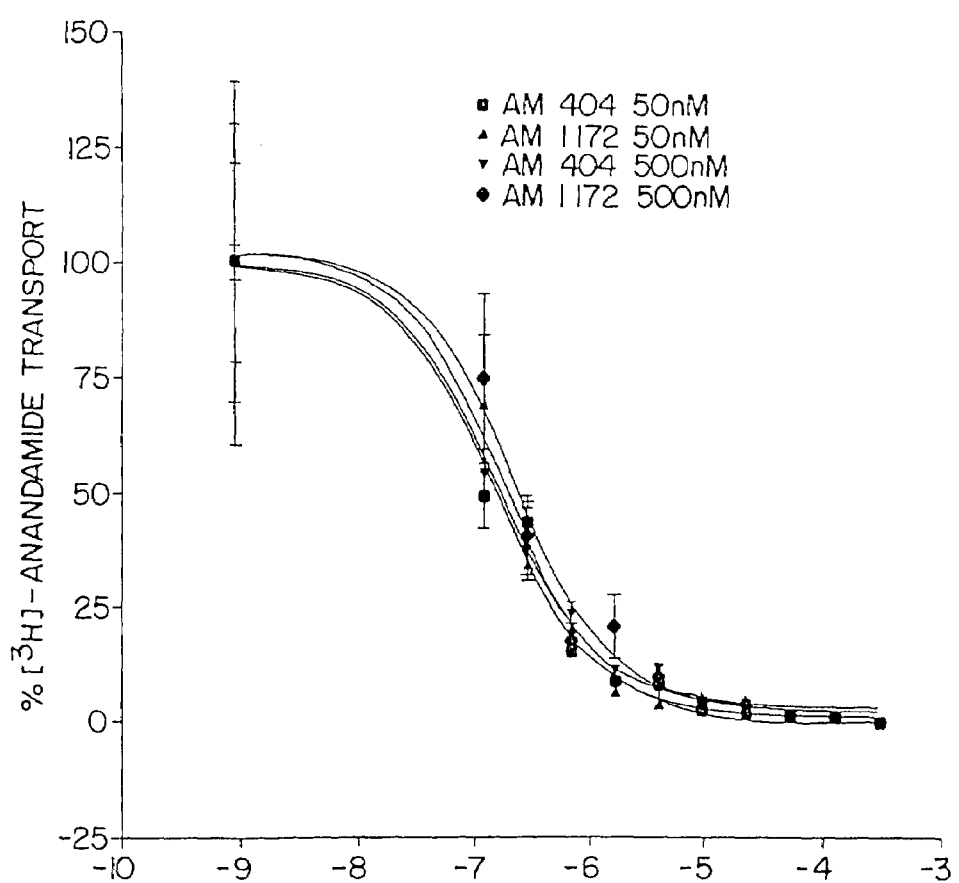
FIG. 2 is a graph similar to FIG. 1 for two different substrate inhibitors.

The $IC_{50}$ data in Table I and Table II provide the affinity data for ligand recognition by the anandamide transporter, but do not provide information on whether the ligands also may serve as substrates for the transporter. To investigate substrate translocation we used a representative set of radioactively labeled compounds. We tested four key analogs that compete with anandamide for uptake: [$^3$H]N-(4-hydroxyphenyl) arachidonamide designated as AM404, and the materials designated AM1172, AM 1177 and AM1191 arachidonylglycerol. As shown in FIGS. 1 and 2, all of the analogs are transported as rapidly and effectively as [$^3$H]anandamide at levels of 50 mM and 500 mM. These findings suggest that the anandamide transporter also may participate in the inactivation of 2-arachidonylglycerol, which was thought to be primarily mediated by enzymatic hydrolysis.

TABLE I

| Structure | $IC_{50}$ |
|---|---|
| AM1191 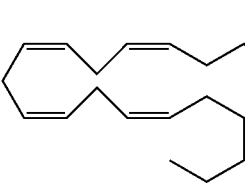 | 0.8 |
| AM1177 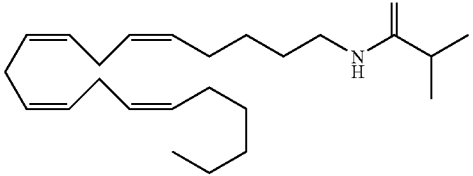 | 5.0 |
| AM1172 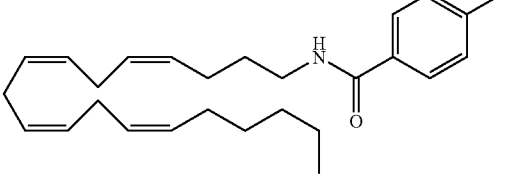 | 2.0 |

TABLE II

| Compound | Structure | $IC_{50}$ (AT inhib.) μM |
|---|---|---|
| 1 | 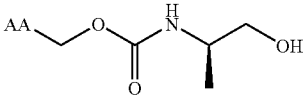 | 7.1 |
| 2 | 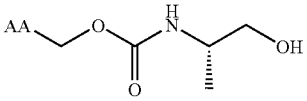 | 6.4 |
| 3 | 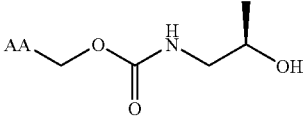 | 1.5 |

TABLE II-continued

| Compound | Structure | IC$_{50}$ (AT inhib.) μM |
|---|---|---|
| 4 | AA-O-C(O)-NH-CH2-CH(OH)-CH3 | 0.4 |
| 5 | AA-O-C(O)-NH-iPr | 21.9 |
| 6 | AA-O-C(O)-NH-cyclopropyl | 15.5 |
| 7 | AA-O-C(O)-NH-cyclobutyl | 15.5 |
| 8 | AA-O-C(O)-NH-cyclohexyl | 33.0 |
| 9 | AA-O-C(O)-NH-C6H4-OH | 6.6 |
| 10 | AA-O-C(O)-NH-thiazoline | 8.6 |
| 11 | AA-O-C(O)-NH-(3-pyridyl) | 16.1 |
| 12 | AA-CH2-NH-C(O)-NH-CH2-CH(OH)-CH3 | 1.78 |
| 13 | OLE-O-C(O)-NH-CH2-CH(OH)-CH3 | 5.92 |
| 14 | LIE-O-C(O)-NH-CH2-CH(OH)-CH3 | 7.21 |
| 15 | LIN-O-C(O)-NH-CH2-CH(OH)-CH3 | 4.50 |
| 16 | AA-CH2-NH-C(O)-O-CH2-CH(OH)-CH3 | 3.29 |
| 17 | AA-C(O)-NH-thiazole | 1.7 |
| 18 | AA-C(O)-NH-thiazoline | 2.8 |
| 19 | AA-C(O)-NH-(1,3,4-thiadiazol-2-yl) | 1.5 |
| 20 | AA-C(O)-NH-benzothiazole | 44.2 |
| 21 | AA-C(O)-NH-(4-Br-thiazol-2-yl) | 92.3 |
| 22 | AA-C(O)-NH-(5-NO2-thiazol-2-yl) | 14.1 |
| 23 | AA-C(O)-NH-(4-Me-thiazol-2-yl) | 11.2 |
| 24 | AA-C(O)-NH-(4,5-diMe-thiazol-2-yl) | 26.0 |
| 25 | AA-C(O)-NH-(4-tBu-thiazol-2-yl) | 24.1 |

TABLE II-continued

| Compound | Structure | IC$_{50}$ (AT inhib.) μM |
|---|---|---|
| AA: | 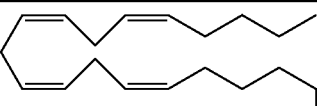 | |
| OLE: | 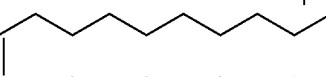 | |
| LIE: | 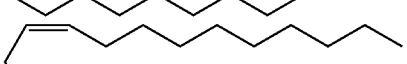 | |
| LIN: | 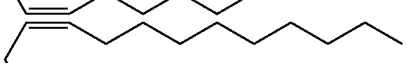 | |

Modifications of the hydrophobic fatty acid tail reveal unexpectedly distinct requirements for recognition and translocation of substrates by the anandamide transporter. Substrate recognition requires the presence of at least one cis double bond situated at the middle of the fatty acid chain, pointing to a preference for ligands in which the hydrophobic tail can fold in the middle and adopt a bent U-shaped conformation. Indeed, analogs with fully saturated chains or those incorporating trans double bonds do not interact significantly with the transporter. By contrast, substrate translocation requires a minimum of four cis nonconjugated double bonds, as ligands containing one, two, or three olefins are transported either very slowly or not at all. This finding suggests that for transmembrane transport to occur substrates must be capable of adopting a tightly folded conformation, one that is not energetically favorable for ligands containing an insufficient number of cis double bonds.

Molecular modeling studies of fatty acid ethanolamides differing in the degree of unsaturation of their hydrophobic carbon chains provides insight into these distinctive conformational requirements. Possible low-energy conformers of these molecules are significantly different. The presence of one or more nonconjugated cis double bonds in the middle of the chain or the use of a biphenyl group leads to the formation of a turn that brings in closer proximity the head and tail of the molecule. The shape of this turn is determined by the number and position of the cis double bonds. Conversely, the introduction of a central trans double bond yields a more extended chain conformation and hinders the ability of the molecule to undergo folding. Thus one of the low-energy conformers of anandamide displays a folded hairpin shape with the two halves of the molecule facing each other. The cis-triene analog may adopt an analogous conformation, though one that is wider than that of anandamide. The width of the turn increases considerably in the cis-dienes and the two monoalkenes due to the marked increase in distance between the head group and tail of the molecule. In the corresponding trans alkene analog, the distance between the head and tail is much greater. It is important to point out that, whereas anandamide like arachidonic acid may adopt either a closed-hairpin or a U-shaped conformation depending on the properties of the surrounding milieu, the hairpin conformation may be thermodynamically unfavorable to fatty acid ethanolamides containing only one or two double bonds.

A plausible interpretation of our results is that recognition and translocation of substrates by the anandamide transporter are governed by distinct conformational preferences. Although the initial recognition step may require that substrates assume a bent U-shaped conformation of variable width, the subsequent step of translocation across the cell membrane may impose a more tightly folded hairpin conformation.

A "therapeutically effective amount" of a compound, as used herein, is the quantity of a compound which, when administered to an individual or animal, results in a sufficiently high level of anandamide in the individual or animal to cause a discernable increase or decrease in a cellular activity affected or controlled by cannabinoid receptors. For example, anandamide can stimulate receptor-mediated signal transduction that leads to the inhibition of forskolin-stimulated adenylate cyclase (Vogel et al., *J. Neurochem.* 60:352 (1993)). Anandamide also causes partial inhibition of N-type calcium currents via a pertussis toxin-sensitive G protein pathway, independently of cAMP metabolism (Mackie et al., *Mol. Pharmacol.* 47:711 (1993)).

A "therapeutically effective amount" of an anandamide inhibitor can also be an amount which results in a sufficiently high level of anandamide in an individual or animal to cause a physiological effect resulting from stimulation of cannabinoid receptors. Physiological effects which result from cannabinoid receptor stimulation include analgesia, decreased nausea resulting from chemotherapy, sedation and increased appetite. Other physiological functions include relieving intraocular pressure in glaucoma patients and suppression of the immune system. Typically, a "therapeutically effective amount" of the compound ranges from about 10 mg/day to about 1,000 mg/day.

As used herein, an "individual" refers to a human. An "animal" refers to veterinary animals, such as dogs, cats, horses, and the like, and farm animals, such as cows, pigs, guinea pigs and the like.

The compounds of the present invention can be administered by a variety of known methods, including orally, rectally, or by parenteral routes (e.g., intramuscular, intravenous, subcutaneous, nasal or topical). The form in which the compounds are administered will be determined by the route of administration. Such forms include, but are not limited to, capsular and tablet formulations (for oral and rectal administration), liquid formulations (for oral, intravenous, intramuscular, subcutaneous, ocular, intranasal, inhalation based or transdermal administration and slow releasing microcarriers (for rectal, intramuscular or intravenous administration). The formulations can also contain a physiologically acceptable vehicle and optional adjuvants, flavorings, colorants and preservatives. Suitable physiologically acceptable vehicles may include saline, sterile water, Ringer's solution, and isotonic sodium chloride solutions. The specific dosage level of active ingredient will depend upon a number of factors, including, for example, biological activity of the particular preparation, age, body weight, sex and general health of the individual being treated.

Those skilled in the art will recognize, or be able to ascertain using no more than routine experimentation, many equivalents to specific embodiments of the invention described specifically herein. Such equivalents are intended to be encompassed in the scope of the invention.

The invention claimed is:

1. A compound having the structure

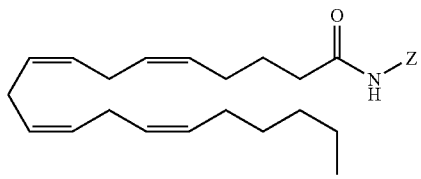

wherein Z is selected from a heterocyclic ring, a substituted heterocyclic ring, a heteroaromatic ring or a substituted heteroaromatic ring.

2. The compound of claim 1 having the structure of any of compounds 17 to 25:

17
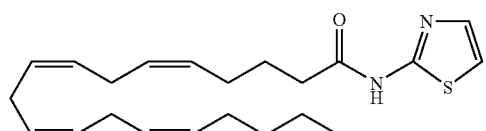

18
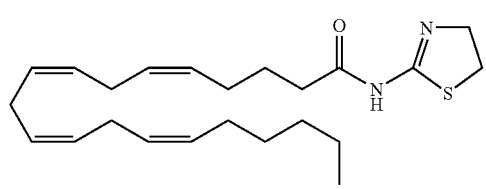

19
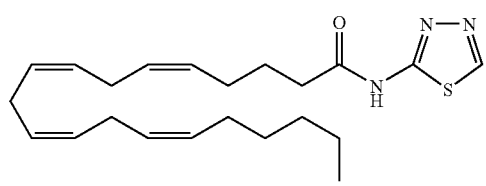

20
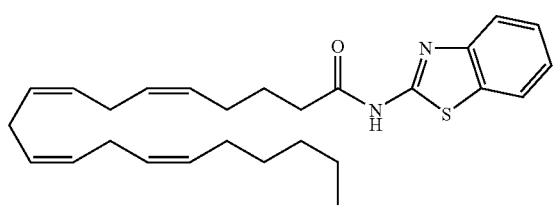

21
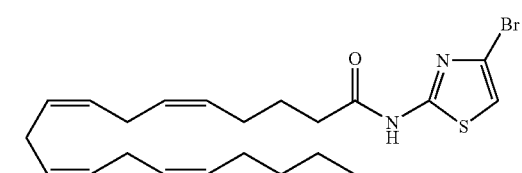

22
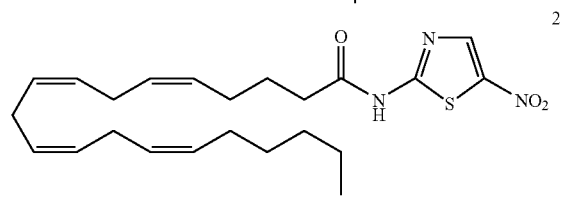

23
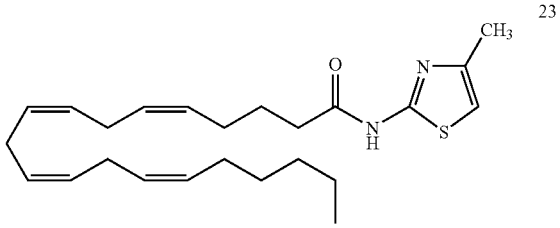

24
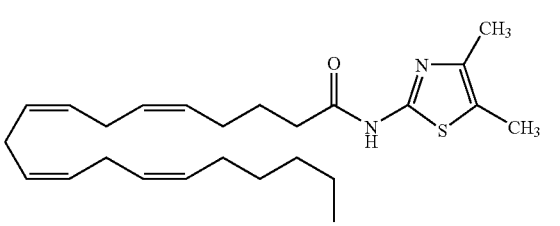

25
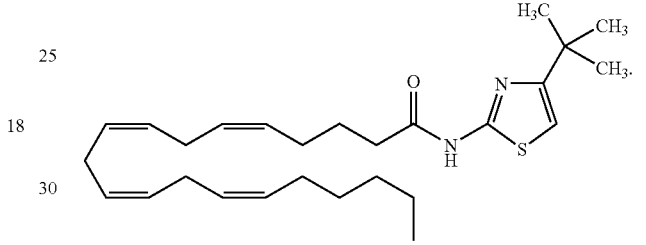

3. A compound selected from the following structures and physiologically acceptable salts thereof:

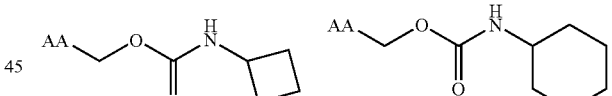

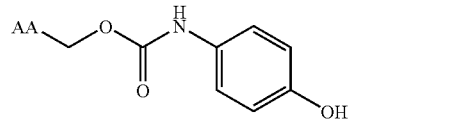

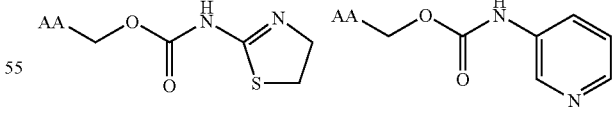

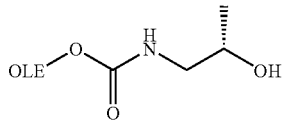

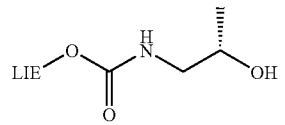

wherein AA is represented by the structure

[structure of arachidonic acid chain],

OLE is represented by the structure

[structure of oleic acid chain],

LIN is represented by the structure

[structure of linolenic acid chain], and

LIE is represented by the structure

[structure of linoleic acid chain].

4. A compound from claim 3 selected from the following structures and physiologically acceptable salts thereof:

[structures showing AA-linked thiazole, thiazoline, thiadiazole, benzothiazole, bromothiazole, nitrothiazole, methylthiazole, dimethylthiazole, and t-butylthiazole amides]

5. A pharmaceutical composition prepared from a compound as disclosed in claim 1.

6. A pharmaceutical composition prepared from a compound as disclosed in claim 3 and physiological acceptable salts thereof.

7. The pharmaceutical composition of claim 6 selected from the following structures and physiologically acceptable salts thereof:

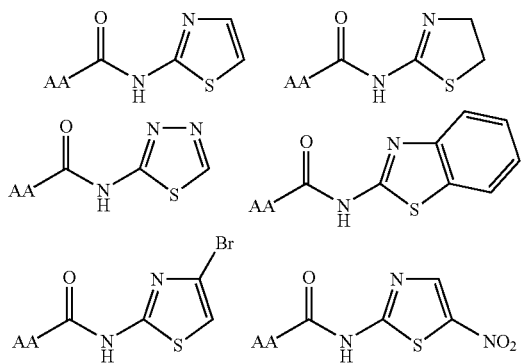
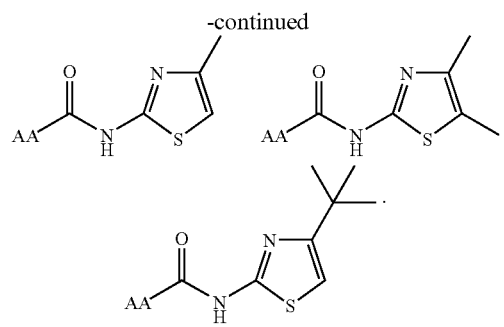
* * * * *